US008673580B2

(12) United States Patent
Tamai et al.

(10) Patent No.: US 8,673,580 B2
(45) Date of Patent: Mar. 18, 2014

(54) AGENT FOR RECRUITMENT OF BONE-MARROW-DERIVED PLURIPOTENT STEM CELL INTO PERIPHERAL CIRCULATION

(75) Inventors: Katsuto Tamai, Osaka (JP); Takehiko Yamazaki, Osaka (JP); Takenao Chino, Osaka (JP); Yasufumi Kaneda, Osaka (JP)

(73) Assignees: Genomix Co., Ltd., Osaka (JP); Osaka University, Osaka (JP)

( * ) Notice: Subject to any disclaimer, the term of this patent is extended or adjusted under 35 U.S.C. 154(b) by 440 days.

(21) Appl. No.: 12/990,047

(22) PCT Filed: Apr. 30, 2009

(86) PCT No.: PCT/JP2009/058515
§ 371 (c)(1),
(2), (4) Date: Jan. 4, 2011

(87) PCT Pub. No.: WO2009/133939
PCT Pub. Date: Nov. 5, 2009

(65) Prior Publication Data
US 2011/0091928 A1    Apr. 21, 2011

(30) Foreign Application Priority Data

Apr. 30, 2008  (JP) ................. 2008-119348

(51) Int. Cl.
*G01N 33/567* (2006.01)
(52) U.S. Cl.
USPC ........................................................ 435/7.21
(58) Field of Classification Search
USPC ........................................................ 435/7.21
See application file for complete search history.

(56) References Cited

U.S. PATENT DOCUMENTS

| | | | |
|---|---|---|---|
| 5,851,986 | A | 12/1998 | Takada et al. |
| 5,902,799 | A | 5/1999 | Herrmann et al. |
| 2002/0058019 | A1 | 5/2002 | Berenson et al. |
| 2003/0003482 | A1 | 1/2003 | Halle et al. |
| 2004/0053841 | A1 | 3/2004 | Tracey et al. |
| 2004/0191246 | A1 | 9/2004 | Connelly et al. |
| 2004/0242481 | A1 | 12/2004 | Bianchi et al. |
| 2004/0265971 | A1 | 12/2004 | Sato et al. |
| 2006/0035851 | A1 | 2/2006 | Bianchi et al. |
| 2006/0111287 | A1 | 5/2006 | Bianchi |
| 2006/0127373 | A1 | 6/2006 | Son et al. |
| 2006/0281674 | A1 | 12/2006 | Tessier et al. |
| 2007/0154529 | A1 | 7/2007 | Bullerdiek |
| 2009/0062187 | A1 | 3/2009 | Bianchi et al. |
| 2009/0202500 | A1 | 8/2009 | Tamai et al. |
| 2011/0097309 | A1 | 4/2011 | Tamai et al. |
| 2011/0104803 | A1 | 5/2011 | Tamai et al. |

FOREIGN PATENT DOCUMENTS

| | | |
|---|---|---|
| AU | 2003/228099 A1 | 1/2004 |
| AU | 2004/203732 A1 | 7/2004 |
| CA | 2325226 | 5/2001 |
| CN | 1671742 A | 9/2005 |
| CN | 101374538 A | 2/2009 |
| EP | 1 114 862 A2 | 7/2001 |
| EP | 1 459 759 A1 | 9/2004 |
| EP | 2055308 A1 | 5/2009 |
| JP | 2001-321434 A | 11/2001 |
| JP | 2003-505506 A | 2/2003 |
| JP | 2005-508913 A | 4/2005 |
| JP | 2005-537253 A | 12/2005 |
| JP | 2006-124389 A | 5/2006 |
| JP | 2006-517537 A | 7/2006 |
| JP | 2006-523085 A | 10/2006 |
| JP | 2008-507505 A | 3/2008 |
| WO | WO 01/08683 A1 | 2/2001 |
| WO | WO 02/074337 A1 | 9/2002 |
| WO | WO 02/088181 A2 | 11/2002 |
| WO | WO 02/092004 A2 | 11/2002 |
| WO | WO 03/043651 A1 | 5/2003 |
| WO | WO 2004/004763 A2 | 1/2004 |
| WO | WO 2004/004763 A3 | 1/2004 |
| WO | WO 2004/061456 A2 | 7/2004 |
| WO | WO 2004/061456 A3 | 7/2004 |
| WO | WO 2005/025604 A2 | 3/2005 |
| WO | WO 2005/074984 A1 | 8/2005 |
| WO | WO 2006/008779 | 1/2006 |
| WO | WO 2006/010628 A1 | 2/2006 |
| WO | WO 2006/047820 A1 | 5/2006 |
| WO | WO 2006/077614 A1 | 7/2006 |
| WO | WO 2006/114805 A2 | 11/2006 |
| WO | WO 2007/015546 A1 | 2/2007 |
| WO | WO 2008/018641 A1 | 2/2008 |
| WO | WO 2008/053892 A1 | 5/2008 |

OTHER PUBLICATIONS

Palumbo et al. "Extracellular HMGB1, a signal of tissue damage, induces mesoangioblast migration and proliferation", JCB, 2004, 164(3):441-449.*
Uchida et al."The chemotactic activity of PDGF-bb, BMP-2, and FGF-2 towards committed and uncommitted mesenchymal stem cells", *The Journal of Japanese Orthopaedic Surgical Society*, 2005, vol. 79, No. 8, S832, 1-P6-6.
Vandal, Karen et al. "Blockade of S100A8 and S100A9 Suppresses Neutrophil Migration in Response to Lipopolysaccharide", *The Journal of Immunology*, Sep. 1, 2003, vol. 171, No. 5, pp. 2602-2609.
Wang, Huan Liang et al. "High mobility group protein B1 and the research progress of its biological effect", *Journal of Chinese Modern Surgery*, Dec. 31, 2006, vol. 3, No. 22, pp. 1806-1809.

(Continued)

Primary Examiner — Bin Shen
(74) Attorney, Agent, or Firm — Saliwanchik, Lloyd & Eisenschenk

(57) ABSTRACT

The present invention for the first time demonstrated that:
(1) bone marrow-derived pluripotent tissue stem cells can be induced in peripheral blood by intravenously administering tissue extract prepared from isolated skin pieces;
(2) the substance in the isolated skin pieces, which is responsible for mobilizing bone marrow-derived pluripotent tissue stem cells to peripheral blood, is HMGB1; and
(3) HMGB1 with the activity of mobilizing bone marrow-derived pluripotent stem cells to peripheral blood can be easily purified from cultured cells.

7 Claims, 14 Drawing Sheets

(56) References Cited

OTHER PUBLICATIONS

Mistry, A.R. et a/. "Recombinant HMG1 Protein Produced in Pichia Pastoris: A Nonviral Gene Delivery Agent" *BioTechniques*, 1997, vol. 22, pp. 718-729.

Alden et al., "In Vivo Endochondral Bone Formation Using a Bone Morphogenetic Protein 2 Adenoviral Vector", *Human Gene Therapy*, 1999, vol. 10, No. 13, pp. 2245-2253.

Bustin, "Regulation of DNA-Dependent Activities by the Functional Motifs of the High-Mobility-Group Chromosomal Proteins". *Molecular and Cellular Biology*, 1999, vol. 19, No. 8, pp. 5237-5246.

Charoonpatrapong et al., "HMGB1 Expression and Release by Bone Cells", *Journal of Cellular Physiology*, 2006, vol. 207, No. 2, pp. 480-490.

Chou et al., "Identity of nuclear high-mobility-group protein, HMG-1, and sulfoglucuronyl carbohydrate-binding protein, SPB-1, in brain". *Journal of Neurochemistry*, 2001, Vol, 77, No. 1, pp. 120-131.

Degryse et ar., "The High Mobility Group (HMG) Boxes of the Nuclear Protein HMG1 Induce Chemotaxis and Cytoskeleton Reorganization in Rat Smooth Muscle Cells", *The Journal of Cell Biology*, 2001, vol. 152, No. 6, pp. 1197-1206.

Delarosa et aL, "Modulation of Adult Mesenchymal Stem Cells Activity by Toll-Like Receptors: Implications on Therapeutic Potential", *Mediators of Inflammation*, 2010, vol. 2010, Article ID: 865601, pp. 1-9.

Eckert et al., "S100 Proteins in the Epidermis", *The Journal of Investigative Dermatology*, 2004, vol. 123, No. 1, pp. 23-33.

Fujii et al., "Roles of Bone Morphogenetic Protein Type I Receptors and Smad Proteins in Osteoblast and Chondroblast Differentiation", *Molecular Biology of the Cell*, 1999, vol. 10, No. 11, pp. 3801-3813.

Germani et al., "Pivotal Advance: High-Mobility group box 1 protein—a cytokine with a role in cardiac repair", *Journal of Leukocyte Biology*, 2007, vol. 81, No. 1, pp. 41-45.

Granero-Molto et al., "Role of mesenchymal stem cells in regenerative medicine: application to bone and cartilage repair", *Expert Opinion on Biological Therapy*, 2008, vol. 8, No. 3, pp. 255-268.

Harris et al., "The nuclear protein HMGB1 as a proinflammatory mediator", *European Journal of Immunology*, 2004, vol. 34, No. 6, pp. 1503-1512.

Harris et al., "Alarmin(g) news about danger", *EMBO reports*, 2006, vol. 7, No. 8, pp. 774-778.

Hori et al., "The Receptor for Advanced Glycation End Products (RAGE) Is a Cellular Binding Site for Amphoterin", *The Journal of Biological Chemistry*, 1995, vol. 270, No. 43, pp. 25752-25761.

Jansen et al., "Transplantation of hematopoietic stem cells from the peripheral blood", *Journal of Cellular and Molecular Medicine*, 2005, vol. 9, No. 1, pp. 37-50.

Jayaraman etal., "High mobility group protein-1 (HMG-1) is a unique activator of p53", *Genes & Development*, 1998, Vo. 12, No. 4. pp. 462-472.

Jiang et al., "Pluripotency of mesenchymal stem cells derived from adult marrow", *Nature*, 2002, vol. 418, No. 6893, pp. 41-49.

Limana et at., "Exogenous High-Mobility Group Box 1 Protein Induces Myocardial Regeneration After Infarction via Enhanced Cardiac C-Kit + Cell Proliferation and Differentiation", *Circulation Research*, 2005, Vo. 97, No. 8, pp. e73-e83.

Liotta et al., "Toll-Like Receptors 3 and 4 Are Expressed by Human Bone Marrow-Derived Mesenchymal Stem Cells and Can Inhibit Their T-Cell Modulatory Activity by Impairing Notch Signaling", *Stem Cells*, 2008, vol. 26, No. 1, pp. 279-289.

Meng et al., "HMGB1 induces migration of human bone marrow-derived mesenchymal stem cells", *Bull Acad. Mil. Med. Sci.*, 2006, vol. 30, No. 3, pp. 213-216. See English Translation.

Merenmies et al., "30-kDa Heparin-binding Protein of Brain (Amphoterin) Involved in Neurite Outgrowth", *The Journal of Biological Chemistry*, 1991, vol. 266, No. 25, pp. 16722-16729.

Müller et al., "The double life of HMGB-1 chromatin protein: architectural factor and extracellular signal", *The EMBO Journal*, 2001, vol. 20, No. 16, pp. 4337-4340.

Nakamura et al., "p38 Mitogen-Activated Protein Kinase Functionally Contributes to Chondrogenesis Induced by Growth/Differentiation Factor-5 in ATDC5 Cells", *Experimental Cell Research*, 1999, vol. 250, No. 2, pp. 351-363.

Opitz et al., "Toll-like Receptor Engagement Enhances the Immunosuppressive Properties of Human Bone Marrow-Derived Mesenchymal Stem Cells by Inducing Indoleamine-2,3-dioxygenase-1 via Interferon-β and Protein Kinase R", *Stem Cells*, 2009, vol. 27, No. 4, pp. 909-919.

Otsuru et al., "BMP-2 mobilizes robust bone marrow mesenchymal progenitor cells to the circulating blood in bone regeneration", *The 28th Annual Meeting of the Molecular Biology Society of Japan*, Nov. 25, 2005, 733(3P-1012). See English Translation.

Palumbo etal., "Extracellular HMGB1, a signal of tissue damage, induces mesoanaioblast migration and proliferation", *The Journal of Cell Biology*, 2004, vol. 164, No. 3, pp. 441-449.

Palumbo et al., "High mobility group box 1 protein, a cue for stem cell recruitment", *Biochemical Pharmacology*, 2004, vol. 68, No. 6, pp. 1165-1170.

Pevsner-Fischer et al., "Toll-like receptors and their ligands control mesenchymal stem cell functions", *Blood*, 2007, vol. 109, No. 4, pp. 1422-1432.

Raicevic etal.. "Inflammation modifies the pattern and the function of Toll-like receptors expressed by human mesenchymal stromal cells", *Human immunology*, 2010, vol. 71, No. 3, pp. 235-244.

Robinson et al., "The S100 Family Heterodimer, MRP-8/14, Binds with High Affinity to Heparin and Heparan Sulfate Glycosaminoglycans on Endothelial Cells", *The Journal of Biological Chemistry*, 2002, vol. 277, No. 5, R29 pp. 3658-3665.

Ryckman et al., "Proinflammatory Activities of S100: Proteins S100A8, S100A9, and S100A8/A9 Induce Neutrophil Chemotaxis adn Adhesion", *The Journal of Immunology*, 2003, vol. 170, NO. 6, pp. 3233-3242.

Schäffer et al., "Wound Fluid Inhibts Wound Fibroblast Nitric Oxide Synhesis", *Journal of Surgical Research*, 2004, vol. 122, No. 1, pp. 43-48.

Shibata et al., "Fibroblast growth-stimulating activity of S100A9 (MRP-14)", *European Journal of Biochemistry*, 2004, vol. 271, No. 11, pp. 2137-2143.

Shing et al., "Heparin Affinity: Purification of a Tumor-Derived Capillary Endothelial Cell Growth Factor", *Science*, 1984, vol. 223, No. 4642, pp. 1296-1299.

Sun et at, "Isolation of Mouse Marrow Mesenchymal Progenitors by a Novel and Reliable Method", *Stem Cells*, 2003, vol. 21, No. 5, pp. 527-535.

Tagami et al., "Elevation of serum high-mobility group box 1 protein during granulocyte colony-stimulating factor-induced peripheral blood stem cell mobilisation", *British Journal of Haematology*, 2006, vol. 135, No. 4, pp. 567-569.

Tamai et al., "New Wave of Wound Healing", *Japanese Journal of Dermatology*, 2008, vol. 118, No. 4, pp. 645, #EL28-4. See English translation.

Tamai et al., U.S. Appl. No. 11/997,475, "Mesenchymal Stem Cell Inducer, Tissue Regeneration Promoter and Method of Preparing Mesenchymal Stem Cell", filed Jan. 31, 2008, Now Abandoned.

Wang et al., "HMG-1 as a Late Mediator of Endotoxin Lethality in Mice", *Science*, 1999, vol. 285, No. 5425, pp. 248-251.

Wu et al., "Mesenchymal Stem Cells Enhance Wound Healing Through Differentiation and Agiogenesis", *Stem Cells*, 2007, vol. 25, No. 10, pp. 2648-2659.

Instruction Manual of HiTrap chelating HP (Amersham Biosciences), 2003, pp. 1-6.

Lonza BenchGuides, "Poietics Human Mesenchymal Stem Cells and Media hMSC", 2008, (Document # TSPT-212-7 Apr. 2008).

Bittira at al., "Mobilization and homing of bone marrow stromal cells in myocardial infarction", *European Journal of Cardio-thoracic Surgery*, Sep. 2003, vol. 24, No. 3, pp. 393-398.

Laflamme et aL "Regenerating the heart", *Nature Biotechnology*, Jul. 2005, vol. 23, No. 7, pp. 845-856.

Maruyama, "Inflammation and HMGB1/RAGE system", *Kekkan Igaku*, 2005, vol. 6, No. 5, pp. 519-525. See English translation.

(56) References Cited

OTHER PUBLICATIONS

"Isolating culture and induced differentiation of marrow mesenchyma stem cells", *Principles and Protocols of Tissue Engineering*, Jun. 2004, pp. 277-278. See English Translation.

Telusma at al., "Dendritic cell activating peptides induce distinct cytokine profiles", *International Immunology*, Nov. 2006, vol. 18, No. 11, pp. 1563-1573.

Kassis, I. et al., "Isolation of mesenchymal stem cells from G-CSF-mobilized human peripheral blood using fibrin microbeads", *Bone Marrow Transplantation*, May 2006, vol. 37, No. 10, pp. 967-976.

Lin, Siang-Yo et al, "The isolation of novel mesenchymal stromal cell chemotactic factors from the conditioned medium of tumor cells", *Experimental Cell Research*, 2008, vol. 314, No. 17, pp. 3107-3117.

Ozaki, Yoshie et al., "Comprehensive Analysis of Chemotactic Factors for Bone Marrow Mesenchymal Stem Cells", *Stem Cells and Development*, Feb. 2007, vol. 16, No. 1, pp. 119-129.

Palumbo, Roberta et al., "Cells migrating to sites of tissue damage in response to the danger signal HMGB1 require NF-κB activation", *The Journal of Cell Biology*, Oct. 8, 2007, vol. 179, No. 1, pp. 33-40.

Sasaki, Mikako et al., "Mesenchymal Stem Cells Are Recruited into Wounded Skin and Contribute to Wound Repair by Transdifferentiation into Multiple Skin Cell Type[1]", *The Journal of Immunology*, Feb. 15, 2008, vol. 180, No. 4, pp. 2581-2587.

U.S. Appl. No. 13/503,329, filed Apr. 20, 2012 (Tamai et al.).

Heil, Matthias et al., "An engineered heparin-binding form of VEGF-E (hbVEGF-E): Biological effects in vitro and mobilization of precursor cells", *Angiogenesis*, 2003, vol. 6, No. 3. pp. 201-211.

Meng, Erhong et al., "High Mobility Group Box 1 Protein Inhibits the Proliferation of Human Mesenchymal Stem Cell and Promotes Their Migration and Differentiation along Osteoblastic Pathway", *Stem Cells and Development*, 2008, vol. 17, No. 4, pp. 805-814.

Pusterla, Tobias et al., "High mobility group B2 is secreted by myeloid cells and has mitogenic and chemoattractant activities similar to high mobility group B1", *Autoimmunity*, Apr. 2009, vol. 42, No. 4, pp. 308-310.

Muhammad, Sajjad. et al. "The HMGBI Receptor Rage Mediates Ischemic Brain Damage," *The Journal of Neuroscience*, Nov. 12, 2008, vol. 28, No. 46, pp. 12023-12031.

Hiratsuka, Sachie et al. "Tumour-mediated upregulation of chemoattractants and recruitment of myeloid cells predetermines lung metastasis," *Nature Cell Biology*, Dec. 2006; Epub Nov. 26, 2006; vol. 8 No. 12, pp. 1369-1375, Supplemental 1-7, Dec. 2006; *Epub* Nov. 26, 2006 (Nature Publishing Group).

Kim, S. etal. "Skin Regeneration Using Keratinocytes and Dermal Fibroblasts Cultured on Biodegradable Microspherical Polymer Scaffolds" *Journal of Biomedical Materials Research Part : Applied Biomaterials*, Nov. 2005, vol. 75, No. 2, pp. 369-377.

Thorey, I. et al. "The $Ca^{2+}$-binding Proteins S100A8 and S100A9 are Encoded by Novel Injury-regulated Genes", *The Journal of Biological Chemistry*, Sep. 21, 2001, vol. 276, No. 38, pp. 35818-35825. (Epub Jul. 19, 2001).

* cited by examiner

CONTROL  MOUSE HEART  MOUSE SKIN

CONTROL  MOUSE BRAIN  MOUSE SKIN

SEQUENCE LISTING

```
<160> NUMBER OF SEQ ID NOS: 18

<210> SEQ ID NO 1
<211> LENGTH: 215
<212> TYPE: PRT
<213> ORGANISM: Homo sapiens

<400> SEQUENCE: 1

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Asp Glu Glu Asp Glu Asp Glu
        195                 200                 205

Glu Glu Asp Asp Asp Asp Glu
    210                 215

<210> SEQ ID NO 2
<211> LENGTH: 648
<212> TYPE: DNA
<213> ORGANISM: Homo sapiens
```

<400> SEQUENCE: 2

```
atgggcaaag gagatcctaa gaagccgaga ggcaaaatgt catcatatgc attttttgtg      60
caaacttgtc gggaggagca taagaagaag cacccagatg cttcagtcaa cttctcagag     120
ttttctaaga agtgctcaga gaggtggaag accatgtctg ctaaagagaa aggaaaattt     180
gaagatatgg caaagcggac aaggcccgt tatgaaagag aaatgaaaac ctatatccct      240
cccaaagggg agacaaaaaa gaagttcaag gatcccaatg cacccaagag gcctccttcg     300
gccttcttcc tcttctgctc tgagtatcgc ccaaaaatca aggagaaca tcctggcctg      360
tccattggtg atgttgcgaa gaaactggga gagatgtgga ataacactgc tgcagatgac     420
aagcagcctt atgaaaagaa ggctgcgaag ctgaaggaaa aatacgaaaa ggatattgct     480
gcatatcgag ctaaggaaa gcctgatgca gcaaaaaagg gagttgtcaa ggctgaaaaa      540
agcaagaaaa agaaggaaga ggaggaagat gaggaagatg aagaggatga ggaggaggag     600
gaagatgaag aagatgaaga tgaagaagaa gatgatgatg atgaataa                  648
```

<210> SEQ ID NO 3
<211> LENGTH: 215
<212> TYPE: PRT
<213> ORGANISM: Mus musculus

<400> SEQUENCE: 3

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Asp Glu Glu
            180                 185                 190

Asp Glu Glu Asp Glu Glu Glu Glu Glu Glu Asp Glu Asp
        195                 200                 205

Glu Glu Asp Asp Asp Asp Glu
    210                 215
```

<210> SEQ ID NO 4
<211> LENGTH: 648
<212> TYPE: DNA
<213> ORGANISM: Mus musculus

<400> SEQUENCE: 4

```
atgggcaaag gagatcctaa aaagccgaga ggcaaaatgt cctcatatgc attctttgtg      60
caaacttgcc gggaggagca caagaagaag cacccggatg cttctgtcaa cttctcagag     120
ttctccaaga agtgctcaga gaggtggaag accatgtctg ctaaagaaaa ggggaaattt     180
gaagatatgg caaaggctga caaggctcgt tatgaaagag aaatgaaaac ctacatcccc     240
cccaaagggg agaccaaaaa gaagttcaag gaccccaatg cacccaagag gcctccttcg     300
gccttcttct tgttctgttc tgagtaccgc cccaaaatca aggcgagca tcctggctta     360
tccattggtg atgttgcaaa gaaactagga gagatgtgga caacactgc agcagatgac     420
aagcagccct atgagaagaa agctgccaag ctgaaggaga gtatgagaa ggatattgct     480
gcctacagag ctaaaggaaa acctgatgca gcgaaaaagg gggtggtcaa ggctgaaaag     540
agcaagaaaa agaaggaaga ggaagatgat gaggaggatg aagaggatga ggaagaggag     600
gaagaagagg aagacgaaga tgaagaagaa gatgatgatg atgaataa                 648
```

<210> SEQ ID NO 5
<211> LENGTH: 215
<212> TYPE: PRT
<213> ORGANISM: Rattus norvegicus

<400> SEQUENCE: 5

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Asp Glu Glu
            180                 185                 190

Asp Glu Glu Asp Glu Glu Glu Glu Glu Glu Asp Glu Asp
        195                 200                 205

Glu Glu Asp Asp Asp Asp Glu
    210                 215
```

<210> SEQ ID NO 6
<211> LENGTH: 648
<212> TYPE: DNA
<213> ORGANISM: Rattus norvegicus

<400> SEQUENCE: 6

```
atgggcaaag gagatcctaa gaagccgaga ggcaaaatgt cctcatatgc attctttgtg      60
caaacctgcc gggaggagca caagaagaag cacccggatg cttctgtcaa cttctcagag     120
ttctccaaga agtgctcaga gaggtggaag accatgtctg ctaaagaaaa ggggaaattt     180
gaagatatgg caaggctgat aaggctcgt tatgaaagag aaatgaaaac ctacatcccc     240
cccaaagggg agaccaaaaa gaagttcaag gaccccaatg cccccaagag gcctccttcg     300
gccttcttct tgttctgttc tgagtaccgc ccaaaaatca aggcgagca tcctggctta      360 tccattggtg atgttgcgaa gaaactagga gagatgtgga caacactgc tgcggatgac      420 aagcagccct atgaaaagaa ggccgccaag ctgaaggaga gtatgagaa ggatattgct      480 gcctacagag ctaaggaaa acctgatgca gcgaaaaagg gggtggtcaa ggctgagaag     540
agcaagaaaa agaaggaaga ggaagacgac gaggaggatg aagaggatga ggaagaggag     600
gaagaggagg aagacgaaga tgaagaagaa gatgatgatg atgaataa                   648
```

<210> SEQ ID NO 7
<211> LENGTH: 209
<212> TYPE: PRT
<213> ORGANISM: Homo sapiens

<400> SEQUENCE: 7

```
Met Gly Lys Gly Asp Pro Asn Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ser Ser Val Asn Phe Ala Glu Phe Ser Lys Lys Cys Ser Glu Arg
        35                  40                  45

Trp Lys Thr Met Ser Ala Lys Glu Lys Ser Lys Phe Glu Asp Met Ala
    50                  55                  60

Lys Ser Asp Lys Ala Arg Tyr Asp Arg Glu Met Lys Asn Tyr Val Pro
65                  70                  75                  80

Pro Lys Gly Asp Lys Lys Gly Lys Lys Lys Asp Pro Asn Ala Pro Lys
                85                  90                  95

Arg Pro Pro Ser Ala Phe Phe Leu Phe Cys Ser Glu His Arg Pro Lys
            100                 105                 110

Ile Lys Ser Glu His Pro Gly Leu Ser Ile Gly Asp Thr Ala Lys Lys
        115                 120                 125

Leu Gly Glu Met Trp Ser Glu Gln Ser Ala Lys Asp Lys Gln Pro Tyr
    130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
            180                 185                 190

Glu Glu Glu Glu Glu Asp Glu Asp Glu Glu Glu Asp Glu Asp Glu
        195                 200                 205

Glu
```

<210> SEQ ID NO 8
<211> LENGTH: 630
<212> TYPE: DNA
<213> ORGANISM: Homo sapiens -continued

```
<400> SEQUENCE: 8
atgggtaaag gagaccccaa caagccgcgg ggcaaaatgt cctcgtacgc cttcttcgtg      60
cagacctgcc gggaagagca caagaagaaa cacccggact cttccgtcaa tttcgcggaa     120
ttctccaaga agtgttcgga gagatggaag accatgtctg caaggagaa gtcgaagttt      180 gaagatatgg caaaaagtga caaagctcgc tatgacaggg agatgaaaaa ttacgttcct     240
cccaaaggtg ataagaaggg gaagaaaaag accccaatg ctcctaaaag gccaccatct     300
gccttcttcc tgttttgctc tgaacatcgc ccaaagatca aaagtgaaca ccctggccta     360
tccattgggg atactgcaaa gaaattgggt gaaatgtggt ctgagcagtc agccaaagat     420
aaacaaccat atgaacagaa agcagctaag ctaaaggaga aatatgaaaa ggatattgct     480
gcatatcgtg ccaagggcaa aagtgaagca ggaaagaagg gccctggcag gccaacaggc     540
tcaaagaaga gaacgaacc agaagatgag gaggaggagg aggaagaaga gatgaagat       600 gaggaggaag aggatgaaga tgaagaataa                                      630
```

<210> SEQ ID NO 9
<211> LENGTH: 210
<212> TYPE: PRT
<213> ORGANISM: Mus musculus

<400> SEQUENCE: 9

```
Met Gly Lys Gly Asp Pro Asn Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ser Ser Val Asn Phe Ala Glu Phe Ser Lys Lys Cys Ser Glu Arg
        35                  40                  45

Trp Lys Thr Met Ser Ala Lys Glu Lys Ser Lys Phe Glu Asp Leu Ala
    50                  55                  60

Lys Ser Asp Lys Ala Arg Tyr Asp Arg Glu Met Lys Asn Tyr Val Pro
65                  70                  75                  80

Pro Lys Gly Asp Lys Lys Gly Lys Lys Asp Pro Asn Ala Pro Lys
                85                  90                  95

Arg Pro Pro Ser Ala Phe Phe Leu Phe Cys Ser Glu Asn Arg Pro Lys
            100                 105                 110

Ile Lys Ile Glu His Pro Gly Leu Ser Ile Gly Asp Thr Ala Lys Lys
        115                 120                 125

Leu Gly Glu Met Trp Ser Glu Gln Ser Ala Lys Asp Lys Gln Pro Tyr
    130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Asn Glu Pro Glu Asp Glu Glu Glu
            180                 185                 190

Glu Glu Glu Glu Glu Glu Glu Glu Asp Asp Glu Glu Glu Glu Asp
        195                 200                 205

Glu Glu
    210
```

<210> SEQ ID NO 10
<211> LENGTH: 633
<212> TYPE: DNA
<213> ORGANISM: Mus musculus

<400> SEQUENCE: 10

```
atgggcaagg gtgaccccaa caagccgcgg ggcaaaatgt cctcgtacgc cttcttcgtg      60
cagacctgcc gcgaggagca caagaagaag catcccgact cgtcggtgaa cttcgccgag     120
ttctccaaga aatgctccga gagatggaag accatgtctg caaggaaaaa gtccaagttt     180
gaagatttgg ccaagagcga caaagctcgt tatgacaggg agatgaagaa ctatgttcct     240
cccaaagggg ataagaaagg aaagaaaaaa gaccccaatg ctccgaagag accaccgtct     300
gccttcttcc tgttttgctc tgaaaatcgc ccaaagatca aaattgaaca cccaggcctg     360
tctattggag atactgcgaa gaaactgggt gagatgtggt ctgagcaatc tgccaaagat     420
aaacaaccgt atgagcagaa agcagctaaa ctaaaggaga agtatgaaaa ggatattgct     480
gcataccgtg ccaagggcaa aagtgaagca ggaagaaagg gtcctggtag gccaacaggc     540
tcaaagaaga agaacgaacc agaagatgag gaggaggaag aagaggagga agaggaggaa     600
gatgacgagg aagaagagga ggatgaagaa taa                                  633
```

<210> SEQ ID NO 11
<211> LENGTH: 210
<212> TYPE: PRT
<213> ORGANISM: Rattus norvegicus

<400> SEQUENCE: 11

```
Met Gly Lys Gly Asp Pro Asn Lys Pro Arg Gly Lys Met Ser Ser Tyr
1               5                   10                  15
Ala Phe Phe Val Gln Thr Cys Arg Glu Glu His Lys Lys Lys His Pro
            20                  25                  30
Asp Ser Ser Val Asn Phe Ala Glu Phe Ser Lys Lys Cys Ser Glu Arg
        35                  40                  45
Trp Lys Thr Met Ser Ala Lys Glu Lys Ser Lys Phe Glu Asp Leu Ala
    50                  55                  60
Lys Ser Asp Lys Ala Arg Tyr Asp Arg Glu Met Lys Asn Tyr Val Pro
65                  70                  75                  80
Pro Lys Gly Asp Lys Lys Gly Lys Lys Asp Pro Asn Ala Pro Lys
                85                  90                  95
Arg Pro Pro Ser Ala Phe Phe Leu Phe Cys Ser Glu His Arg Pro Lys
            100                 105                 110
Ile Lys Ser Glu His Pro Gly Leu Ser Ile Gly Asp Thr Ala Lys Lys
        115                 120                 125
Leu Gly Glu Met Trp Ser Glu Gln Ser Ala Lys Asp Lys Gln Pro Tyr
    130                 135                 140
Glu Gln Lys Ala Ala Lys Leu Lys Glu Lys Tyr Glu Lys Asp Ile Ala
145                 150                 155                 160
Ala Tyr Arg Ala Lys Gly Lys Ser Glu Val Gly Lys Lys Gly Pro Gly
                165                 170                 175
Arg Pro Thr Gly Ser Lys Lys Lys Asn Glu Pro Glu Asp Glu Glu Glu
            180                 185                 190
Glu Glu Glu Glu Glu Asp Asp Glu Asp Glu Glu Glu Asp Glu Asp
        195                 200                 205
Glu Glu
    210
```

<210> SEQ ID NO 12
<211> LENGTH: 633
<212> TYPE: DNA
<213> ORGANISM: Rattus norvegicus

<400> SEQUENCE: 12

```
atgggcaagg gggaccccaa caagccgcgg ggcaagatgt cctcgtacgc cttcttcgtg      60
cagacctgcc gggaggagca caagaagaag catcccgact cgtcggtcaa cttcgccgag     120
ttctcgaaga aatgttcgga gagatggaag accatgtctg ccaaggaaaa gtcgaagttt     180
gaggatttgg ccaagagcga caaagctcgt tatgacaggg agatgaagaa ctatgttcct     240
cccaaaggtg ataagaaagg aaagaaaaaa gatccaaatg ctcccaagag accaccgtct     300
gccttcttcc tgttttgctc tgaacatcgc ccaaagatca aaagtgaaca ccccggcctg     360
tctattggag atactgcaaa gaactgggg gagatgtggt ctgagcaatc tgccaaagat     420
aaacaaccgt atgagcagaa agcagctaaa ctaaaggaga gtatgaaaaa ggatattgct     480
gcataccgtg ccaagggcaa aagtgaagta ggaaagaagg gtcctggtag gccaacaggc     540
tcaaagaaga gaatgaacc agaagatgag gaagaggagg aggaggaaga gatgatgaa      600
gatgaagagg aggaagatga ggatgaagaa taa                                  633
```

<210> SEQ ID NO 13
<211> LENGTH: 200
<212> TYPE: PRT
<213> ORGANISM: Homo sapiens

<400> SEQUENCE: 13

```
Met Ala Lys Gly Asp Pro Lys Lys Pro Lys Gly Lys Met Ser Ala Tyr
  1               5                  10                  15
Ala Phe Phe Val Gln Thr Cys Arg Glu Glu His Lys Lys Lys Asn Pro
             20                  25                  30
Glu Val Pro Val Asn Phe Ala Glu Phe Ser Lys Lys Cys Ser Glu Arg
         35                  40                  45
Trp Lys Thr Met Ser Gly Leu Glu Lys Ser Lys Phe Asp Glu Met Ala
     50                  55                  60
Lys Ala Asp Lys Val Arg Tyr Asp Arg Glu Met Lys Asp Tyr Gly Pro
 65                  70                  75                  80
Ala Lys Gly Gly Lys Lys Lys Asp Pro Asn Ala Pro Lys Arg Pro
                 85                  90                  95
Pro Ser Gly Phe Phe Leu Phe Cys Ser Glu Phe Arg Pro Lys Ile Lys
            100                 105                 110
Ser Thr Asn Pro Gly Ile Ser Ile Gly Asp Val Ala Lys Leu Gly
        115                 120                 125
Glu Met Trp Asn Asn Leu Asn Asp Ser Glu Lys Gln Pro Tyr Ile Thr
    130                 135                 140
Lys Ala Ala Lys Leu Lys Glu Lys Tyr Glu Lys Asp Val Ala Asp Tyr
145                 150                 155                 160
Lys Ser Lys Gly Lys Phe Asp Gly Ala Lys Gly Pro Ala Lys Val Ala
                165                 170                 175
Arg Lys Lys Val Glu Glu Glu Asp Glu Glu Glu Glu Glu Glu Glu Glu
            180                 185                 190
Glu Glu Glu Glu Glu Glu Asp Glu
        195                 200
```

<210> SEQ ID NO 14
<211> LENGTH: 603
<212> TYPE: DNA
<213> ORGANISM: Homo sapiens

<400> SEQUENCE: 14

```
atggctaaag gtgaccccaa gaaaccaaag ggcaagatgt ccgcttatgc cttctttgtg      60
```

```
cagacatgca gagaagaaca taagaagaaa aacccagagg tccctgtcaa ttttgcggaa      120
ttttccaaga agtgctctga gaggtggaag acgatgtccg ggaaagagaa atctaaattt      180
gatgaaatgg caaaggcaga taaagtgcgc tatgatcggg aaatgaagga ttatggacca      240
gctaagggag gcaagaagaa gaaggatcct aatgctccca aaaggccacc gtctggattc      300
ttcctgttct gttcagaatt ccgccccaag atcaaatcca aaacccecgg catctctatt      360 ggagacgtgg caaaaaagct gggtgagatg tggaataatt taaatgacag tgaaaagcag      420
ccttacatca ctaaggcggc aaagctgaag gagaagtatg agaaggatgt tgctgactat      480
aagtcgaaag gaaagtttga tggtgcaaag ggtcctgcta agttgcccg gaaaaaggtg      540 gaagaggaag atgaagaaga ggaggaggaa gaagaggagg aggaggagga ggaggatgaa      600
taa                                                                   603
```

<210> SEQ ID NO 15
<211> LENGTH: 200
<212> TYPE: PRT
<213> ORGANISM: Mus musculus

<400> SEQUENCE: 15

```
Met Ala Lys Gly Asp Pro Lys Pro Lys Gly Lys Met Ser Ala Tyr
1               5                   10                  15

Ala Phe Phe Val Gln Thr Cys Arg Glu Glu His Lys Lys Lys Asn Pro
                20                  25                  30

Glu Val Pro Val Asn Phe Ala Glu Phe Ser Lys Lys Cys Ser Glu Arg
            35                  40                  45

Trp Lys Thr Met Ser Ser Lys Glu Lys Ser Lys Phe Asp Glu Met Ala
        50                  55                  60

Lys Ala Asp Lys Val Arg Tyr Asp Arg Glu Met Lys Asp Tyr Gly Pro
65                  70                  75                  80

Ala Lys Gly Gly Lys Lys Lys Asp Pro Asn Ala Pro Lys Arg Pro
                85                  90                  95

Pro Ser Gly Phe Phe Leu Phe Cys Ser Glu Phe Arg Pro Lys Ile Lys
            100                 105                 110

Ser Thr Asn Pro Gly Ile Ser Ile Gly Asp Val Ala Lys Lys Leu Gly
        115                 120                 125

Glu Met Trp Asn Asn Leu Ser Asp Asn Glu Lys Gln Pro Tyr Val Thr
130                 135                 140

Lys Ala Ala Lys Leu Lys Glu Lys Tyr Glu Lys Asp Val Ala Asp Tyr
145                 150                 155                 160

Lys Ser Lys Gly Lys Phe Asp Gly Ala Lys Gly Pro Ala Lys Val Ala
                165                 170                 175

Arg Lys Lys Val Glu Glu Glu Glu Glu Glu Glu Glu Glu Glu Glu
            180                 185                 190

Glu Glu Glu Glu Glu Glu Asp Glu
        195                 200
```

<210> SEQ ID NO 16
<211> LENGTH: 603
<212> TYPE: DNA
<213> ORGANISM: Mus musculus

<400> SEQUENCE: 16

```
atggctaaag gtgaccccaa gaaaccaaag ggcaagatgt ctgcttatgc cttctttgtg       60
cagacatgca gggaagaaca taagaagaaa aacccagagg ttcccgtcaa ttttgctgag      120
```

```
ttctccaaga agtgctcgga gaggtggaag accatgtcta gcaaagagaa atcaaagttt    180
gatgaaatgg caaaggcaga taaagtccga tatgatcggg agatgaaaga ttatggacca    240
gctaaaggag gcaagaagaa gaaggaccca aatgccccca aaagacctcc gtctggattt    300
ttcttattct gctctgaatt ccgcccaag atcaaatcca caaaccctgg catctccatt     360
ggagatgtgg caaaaaagct gggtgagatg tggaataact taagtgacaa tgaaaagcag    420
ccttatgtca ccaaggcagc aaagctgaag gagaagtatg agaaggatgt tgctgactat    480
aagtctaaag ggaagtttga tggtgccaag ggtcctgcta aagttgcccg gaaaaaggtg    540
gaagaagagg aagaggagga ggaagaggaa gaagaggagg aggaagagga ggaagatgaa    600
taa                                                                  603

<210> SEQ ID NO 17
<211> LENGTH: 63
<212> TYPE: DNA
<213> ORGANISM: Artificial
<220> FEATURE:
<223> OTHER INFORMATION: An artificially synthesized nucleotide sequence

<400> SEQUENCE: 17
atgcagacag acacactcct gctatgggta ctgctgctgt gggttccagg ttccactggt     60
gac                                                                   63

<210> SEQ ID NO 18
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 18

Asp Tyr Lys Asp Asp Asp Lys
1               5
```

AGENT FOR RECRUITMENT OF BONE-MARROW-DERIVED PLURIPOTENT STEM CELL INTO PERIPHERAL CIRCULATION

CROSS REFERENCE TO A RELATED APPLICATION

This application is a National Stage Application of International Application Number PCT/JP2009/058515, filed Apr. 30, 2009; which claims priority to Japanese Patent Application No. 2008-119348, filed Apr. 30, 2008; which are incorporated herein by reference in their entirety.

TECHNICAL FIELD

The present invention relates to agents that mobilize bone marrow-derived pluripotent stem cells into peripheral circulation.

BACKGROUND ART

In recent years, it has been revealed that various stem cells contribute towards the repairing process of damaged tissues, and development of novel regenerative medicines that induce functional tissue regeneration by mobilizing a large number of stem cells to lesion sites is in progress. To bring these novel regenerative medicines to realization, (i) stem cells that are mobilizable to lesion sites must be present abundantly in vivo; and (ii) factors that mobilize stem cells to lesion sites must be isolated/identified.

Examples of stem cells that are mobilizable to lesion sites include tissue stem cells present in lesion areas or nearby tissues, and bone marrow-derived stem cells present in peripheral blood. In recent years, it has been reported that bone marrow-derived cells contribute to many types of damaged tissue regenerations, but the mechanism for mobilizing bone marrow-derived cells to lesion sites is unknown. Bone marrow-derived cells as used herein are distinguished from hematopoietic stem cells which have the potential to differentiate into blood cells (leukocytes and erythrocytes), and include stem cells represented by cells called bone marrow mesenchymal stem cells, or tissue progenitor cell groups present in the bone marrow. Bone marrow mesenchymal stem cells are undifferentiated stem cells with the potential to differentiate into osteoblasts, adipocytes, and chondrocytes, and can further differentiate into other mesenchymal cells such as fibroblasts, muscle cells, stromal cells, and tendon cells. Recently, it has been proved that bone marrow mesenchymal stem cells differentiate into nerve cells and further to epithelial cells (such as skin keratinocytes) and vascular endothelial cells (Non-patent Document 9). Tissue progenitor cells are defined as undifferentiated cells having a unidirectional potential to differentiate into specific tissues/cells other than those of the blood system, and include undifferentiated cells with the potential to differentiate into mesenchymal tissue, epithelial tissue, nerve tissue, parenchymatous organs, and vascular endothelium, as mentioned above.

HMGB1 (High Mobility Group Box 1: High mobility group 1 protein) is a protein with molecular weight of about 25,000 that exists in almost all types of cells in vivo. According to previous reports, the following functions are known:
1) HMGB1 regulates gene expression by intracellularly binding with DNA to control chromatin structure (Non-patent Document 1);
2) HMGB1 is secreted from monocytes or macrophages present in inflammatory tissues by the action of inflammatory cytokines TNF-$\alpha$, IL-1, and LPS, and extracellularly binds to RAGE (Receptor for Advanced Glycation End products) (Non-patent Document 2) to induce strong inflammatory reactions (Non-patent Document 3);
3) HMGB1 is released from hypoperfusion-induced necrosed cells into surrounding tissues (Non-patent Document 4);
4) HMGB1 is associated with the progression of inflammation in patients with septicemia, a severe infectious disease (Non-patent Document 5);
5) administration of HMGB1 to infarcted areas in a myocardial infarction model promotes the division/proliferation of stem cells present in the myocardium, and therefore the regeneration/functional recovery of the myocardium (Patent Document 1);
6) administration of HMGB1 to a model animal with hypoperfusive liver failure prior to the induction of hypoperfusive conditions alleviates the degree of hepatic impairment (Non-patent Document 6);
7) administration of HMGB1 to lesion sites in a muscle injury model directs simultaneously-administered vascular progenitor cells to lesion sites, and therefore promotes muscular tissue regeneration (Non-patent Document 7); and
8) HMGB1 induces neurite formation in nerve cells (Non-patent Document 8). However, no previous reports showed that bone marrow-derived stem cells, in particular those mesenchymal stem cells that can differentiate into osteoblasts, chondrocytes, adipocytes, and the like, are mobilized to damaged tissues.

Conventionally it was thought that central nerve cells in the brain and spinal cord cannot be regenerated once damaged. However, recently the existence of neural stem cells became known and induction of these cells was made possible. The neural stem cell niche within the nominal nerve system has also been identified. Therefore, recovery of damaged central neurons, which was long considered impossible, is now expected to be feasible. Currently, research related to neuronal regeneration for brain and spinal cord injury, degenerative diseases, and the like is being expanded.

The main causes of brain tissue (cells) injury are traumatic cerebral contusion and cerebral ischemic diseases. Other causes can be injury resulting from brain surgeries such as brain tumor removal. In particular, complete removal of neuroglioma that have developed from cerebral parenchymal cells is difficult, and there is no choice but to stop at partial removal to avoid damage to motor and language functions. Moreover, malignant neuroglioma has a worse prognosis, and none of the treatments of active research in recent years ranging from chemotherapy and radiotherapy to immunotherapy/gene therapy has achieved satisfactory effects. Accordingly, an ideal treatment would be one that can remove as many tumor cells as possible, and restore damage to cerebral functions that results from the removal.

PRIOR ART DOCUMENTS

Patent Documents

[Patent Document 1] Japanese Patent Application Kohyo Publication No. (JP-A) 2005-537253 (unexamined Japanese national phase publication corresponding to a non-Japanese international publication)

Non-patent Documents

[Non-patent Document 1] Bustin et al., Mol Cell Biol, 19: 5237-5246, 1999

[Non-patent Document 2] Hori et al., J. Biol. Chem., 270, 25752-25761, 1995

[Non-patent Document 3] Wang et al., Science, 285: 248-251, 1999

[Non-patent Document 4] Muller et al., EMBO J, 20: 4337-4340, 2001

[Non-patent Document 5] Wang et al., Science, 285: 248-251, 1999

[Non-patent Document 6] Germani et al., J. Leukoc. Biol., Jan; 81(1): 41-5, 2007

[Non-patent Document 7] Palumbo et al., J. Cell Biol., 164: 441-449, 2004

[Non-patent Document 8] Merenmies et al., J. Biol. Chem., 266: 16722-16729, 1991

[Non-patent Document 9] Wu Y et al., Stem cells, 25:2648-2659, 2007

DISCLOSURE OF THE INVENTION

Problems to be Solved by the Invention

It is known that mesenchymal stem cells capable of differentiating into bone tissues, cartilage tissues, and adipose tissues exist among stem cells in bone marrow. In recent years, it has been revealed that pluripotent stem cells that differentiate into epithelial cells and neural cells exist.

Meanwhile, methods for treating intractable cutaneous ulcer include treatments by skin grafting. Studies of the present inventors have revealed that the skin is regenerated through reconstruction of epidermis, dermis, hair follicles (tissue constituting the hair), and such from bone marrow-derived cells in grafted skin after ulcer treatment. Thus, there is an expectation that a simple and efficient method for collecting such cell populations with tissue-repairing ability from the bone marrow may be established. To date, however, such method still remains to be developed.

Thus, an objective of the present invention is to provide methods for mobilizing a large number of bone marrow-derived pluripotent stem cells into peripheral blood.

Means for Solving the Problems

There is a possibility that during the survival process of a grafted skin on biological tissue, bone marrow-derived cells are mobilized to the skin graft from non-skin tissue and thus participate in skin tissue regeneration. This suggests a potential mechanism for mobilizing such pluripotent bone marrow-derived cells to peripheral blood. The present invention enables to mobilize a large number of bone marrow-derived pluripotent stem cells into peripheral blood by intravenously administering a skin tissue extract or bone marrow-derived pluripotent stem cell inducer. Specifically, the present invention revealed for the first time in the world that:

(1) bone marrow-derived pluripotent tissue stem cells can be induced in peripheral blood by intravenously administering a tissue extract prepared from isolated skin pieces;

(2) the substance in isolated skin pieces, which is responsible for mobilizing bone marrow-derived pluripotent tissue stem cells to peripheral blood, is HMGB1; and (3) HMGB1 that has the activity of mobilizing bone marrow-derived pluripotent stem cells to peripheral blood can be easily purified from cultured cells.

Based on the findings described above, the present invention provides the following inventions:

[1] an agent for mobilizing a bone marrow cell to peripheral blood from bone marrow, which is administered to blood vessel or muscle, and which comprises the component of any one of:

(a) an HMGB1 protein;
(b) a cell that secretes an HMGB1 protein;
(c) a vector inserted with a DNA encoding an HMGB1 protein;
(d) an HMGB2 protein;
(e) a cell that secretes an HMGB2 protein;
(f) a vector inserted with a DNA encoding an HMGB2 protein;
(g) an HMGB3 protein;
(h) a cell that secretes an HMGB3 protein; and
(i) a vector inserted with a DNA encoding an HMGB3 protein;

[2] an agent for mobilizing a bone marrow cell to peripheral blood from bone marrow, which is produced by a method comprising the step of immersing a cell or tissue in a solvent, and which is administered to blood vessel or muscle;

[3] an agent for mobilizing a bone marrow cell to peripheral blood from bone marrow, which is administered to blood vessel or muscle, and which comprises a heparin-binding fraction produced by a method comprising the steps of:

(a) immersing a cell or tissue in a solvent;
(b) contacting immobilized heparin with an extract prepared in step (a); and
(c) eluting a heparin-binding fraction from the immobilized heparin;

[4] a method for assessing whether or not a factor that mobilizes a bone marrow cell to peripheral blood from bone marrow is contained in an extract of a cell or tissue, and for determining that the factor is contained in the extract of cell or tissue when the activity of mobilizing a bone marrow cell to peripheral blood from bone marrow in step (b) is higher than that of the control, wherein the method comprises the steps below:

(a) preparing a cell extract; and
(b) measuring the activity of mobilizing a bone marrow cell to peripheral blood from bone marrow in the extract prepared in step (a);

[5] a method of screening for an extract of a cell or tissue containing a factor that mobilizes a bone marrow cell to peripheral blood from bone marrow, which comprises the steps of:

(a) assessing multiple extracts by the method of [4] on whether or not a factor that mobilizes a bone marrow cell to peripheral blood from bone marrow is contained in the extract; and
(b) selecting an extract which is assessed to contain a factor that mobilizes a bone marrow cell to peripheral blood from bone marrow by step (a);

[6] a method for identifying a factor that mobilizes a bone marrow cell to peripheral blood from bone marrow, which comprises the step of purifying a factor that mobilizes a bone marrow cell to peripheral blood from bone marrow from an extract that is determined to contain a factor that mobilizes a bone marrow cell to peripheral blood from bone marrow by the method of [4] or [5], using the activity of mobilizing a bone marrow cell to peripheral blood from bone marrow as an indicator;

[7] a kit for mobilizing a bone marrow cell to peripheral blood from bone marrow, comprising a composition to be administered to blood vessel or muscle and which comprises the substance of any one of:

(a) an HMGB1 protein;
(b) a cell that secretes an HMGB1 protein;
(c) a vector inserted with a DNA encoding an HMGB1 protein;
(d) an HMGB2 protein;

(e) a cell that secretes an HMGB2 protein;
(f) a vector inserted with a DNA encoding an HMGB2 protein;
(g) an HMGB3 protein;
(h) a cell that secretes an HMGB3 protein; and
(i) a vector inserted with a DNA encoding an HMGB3 protein;

[8] a kit for mobilizing a bone marrow cell to peripheral blood from bone marrow, comprising a extract of a cell or tissue to be administered to blood vessel or muscle and which is produced by a method comprising the step of immersing a cell or tissue in a solvent;

[9] a kit for mobilizing a bone marrow cell to peripheral blood from bone marrow, comprising a heparin-binding fraction to be administered to blood vessel or muscle and which is produced by a method comprising the steps of:
(a) immersing a cell or tissue in a solvent;
(c) eluting a heparin-binding fraction from the immobilized heparin;

[10] a method for mobilizing a bone marrow cell to peripheral blood from bone marrow, comprising the step of administering to blood vessel or muscle the substance of any one of:
(a) an HMGB1 protein;
(b) a cell that secretes an HMGB1 protein;
(c) a vector inserted with a DNA encoding an HMGB1 protein;
(d) an HMGB2 protein;
(e) a cell that secretes an HMGB2 protein;
(f) a vector inserted with a DNA encoding HMGB2 protein;
(g) an HMGB3 protein;
(h) a cell that secretes an HMGB3 protein; and
(i) a vector inserted with a DNA encoding an HMGB3 protein;

[11] a method for mobilizing a bone marrow cell to peripheral blood from bone marrow, which comprises the step of administering to blood vessel or muscle an extract of a cell or tissue prepared by a method comprising the step of immersing a cell or tissue in a solvent;

[12] a method for mobilizing a bone marrow cell to peripheral blood from bone marrow, comprising the step of administering to blood vessel or muscle a heparin-binding fraction prepared by a method comprising the steps of:
(a) immersing a cell or tissue in a solvent;
(b) contacting immobilized heparin with the extract prepared in step (a): and
(c) eluting a heparin-binding fraction from the immobilized heparin;

[13] use of any one of the following substances (a) to (i) in the production of and agent for mobilizing a bone marrow cell to peripheral blood from bone marrow, which is administered to blood vessel of muscle:
(a) an HMGB1 protein;
(b) a cell that secretes an HMGB1 protein;
(c) a vector inserted with a DNA encoding an HMGB1 protein;
(d) an HMGB2 protein;
(e) a cell that secretes an HMGB2 protein;
(f) a vector inserted with a DNA encoding an HMGB2 protein;
(g) an HMGB3 protein;
(h) a cell that secretes an HMGB3 protein; and
(i) a vector inserted with a DNA encoding an HMGB3 protein;

[14] use of an extract of a cell or tissue produced by a method comprising the step of immersing a cell or tissue in a solvent, in the preparation of an agent for mobilizing a bone marrow cell to peripheral blood from bone marrow, which is to be administered to blood vessel or muscle;

[15] use of a heparin-binding fraction produced by a method comprising the steps of:
(a) immersing a cell or tissue in a solvent;
(b) contacting immobilized heparin with the extract prepared in step (a): and
(c) eluting a heparin-binding fraction from the immobilized heparin; in the preparation of an agent for mobilizing a bone marrow cell to peripheral blood from bone marrow, which is to be administered to blood vessel or muscle;

[16] the substance of any one of:
(a) an HMGB1 protein;
(b) a cell that secretes an HMGB1 protein;
(c) a vector inserted with a DNA encoding an HMGB1 protein;
(d) an HMGB2 protein;
(e) a cell that secretes an HMGB2 protein;
(f) a vector inserted with a DNA encoding an HMGB2 protein;
(g) an HMGB3 protein;
(h) a cell that secretes an HMGB3 protein; and
(i) a vector inserted with a DNA encoding an HMGB3 protein;
which is used in a method for mobilizing a bone marrow cell to peripheral blood from bone marrow, which is to be administered to blood vessel or muscle;

[17] an extract of a cell or tissue produced by a method comprising the step of immersing a cell or tissue in a solvent, which is used in a method for mobilizing a bone marrow cell to peripheral blood from bone marrow, and which is to be administered to blood vessel or muscle; and

[18] a heparin-binding fraction produced by a method comprising the steps of:
(a) immersing a cell or tissue in a solvent;
(b) contacting immobilized heparin with the extract prepared in step (a); and
(c) eluting a heparin-binding fraction from the immobilized heparin;
which is used in a method for mobilizing a bone marrow cell to peripheral blood from bone marrow, and which is to be administered into blood vessel or muscle.

MODE FOR CARRYING OUT THE INVENTION

Figure 1:
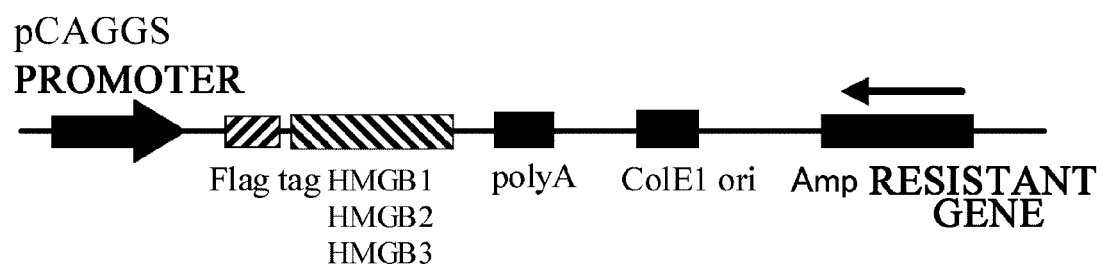
FIG. 1 presents a diagram showing an HMGB1 expression vector.

The present invention provides pharmaceutical agents for mobilizing bone marrow cells to peripheral blood from bone marrow, comprising any one of the following ingredients (a) to (i), which is to be administered to peripheral blood or muscle:

(a) an HMGB1 protein;
(b) a cell secreting an HMGB1 protein;
(c) a vector inserted with a DNA which encodes an HMGB1 protein;
(d) an HMGB2 protein;
(e) a cell secreting an HMGB2 protein;
(f) a vector inserted with a DNA which encodes an HMGB2 protein;
(g) an HMGB3 protein;
(h) a cell secreting an HMGB3 protein; and
(i) a vector inserted with a DNA which encodes an HMGB3 protein.

Bone marrow tissue stem cells are mobilized into peripheral circulation by administering the above-described pharmaceutical agents to blood vessel or muscle, and thus regeneration of the damaged tissue can be promoted. Further, besides the use of an above pharmaceutical agent as an inducer/promoter of functional tissue regeneration, its use as a so-called preventive drug which prevents deteriorations in tissue/organ functions caused by the reduction of tissue stem cells, or as an anti-aging drug which delays the progress of age-related alterations is anticipated.

Alternatively, such treatment can be achieved by administering the above-described pharmaceutical agent, collecting and concentrating the pluripotent stem cells mobilized to peripheral blood outside the body, and administering the cells to lesion sites. Conventional therapy using bone marrow mesenchymal stem cells is invasive because cells are collected from the bone marrow located deeply inside the body. Meanwhile, by using the pharmaceutical agents of the present invention, bone marrow mesenchymal stem cells can be collected from peripheral blood in a less-invasive fashion and used for cell transplantation or such.

The present invention relates to pharmaceutical agents for mobilizing bone marrow cells to peripheral blood from bone marrow, which comprise extracts of cells or tissues to be administered to blood vessel or muscle and that are prepared by methods comprising the step of immersing cells or tissues in a solvent.

Cells or tissues to be immersed in a solvent are not specifically limited, and examples include tissue-derived cells and cell lines established from tissue-derived cells (such as HeLa and HEK293, but not limited thereto), isolated cells, non-isolated cells (such as cells existing in isolated tissues), cells introduced with a DNA encoding an HMGB1, HMGB2, or HMGB3 protein. Any tissue may be used as the tissue described as above. For example, such tissues include, but are not limited to, living skin tissues or tissues obtained from internal biopsies (operations) (such as brain, lung, heart, liver, stomach, small intestine, large intestine, pancreas, kidney, bladder, spleen, uterus, testis, and blood).

Examples of the above solvent include, but are not limited to, physiological saline, PBS (phosphate-buffered saline), and TBS (Tris-buffered saline). Moreover, the immersion time of cells or tissue in a solvent should be a duration necessary and sufficient for inducing cell necrosis, that is, 1 hour to 48 hours (such as 6 to 48 hours), and preferably 12 to 24 hours, but is not limited thereto. Therefore, the "step of immersing cells in a solvent" can be rephrased as "step of immersing cells in a solvent for a duration necessary and sufficient for inducing necrosis" or "step of necrosing cells". Moreover, examples of the temperature for immersing cells or tissue in a solvent include, but are not limited to, 4° C. to 25° C. (such as 4° C. to 8° C.), and preferably 4° C. Further, examples of the pH for immersing cells or tissue in a solvent include, without limitation, pH 7 to 8, and preferably pH 7.5. Examples of the buffer include, without limitation, a phosphate buffer solution at a concentration of 10 mM to 50 mM, preferably 10 to 20 mM.

Moreover, in the present invention, cells or tissues can be removed from a solvent containing them after they are immersed in the solvent. The method for removing cells or tissues from a solvent is not particularly limited as long as the method is well known to those skilled in the art. For example, cells or tissues can be removed from a solvent by centrifuging at a gravity acceleration of 10 G to 100,000 G (for example, 440 G) at 4° C. to 25° C. (for example, 4° C.), followed by separation of the supernatant, but the removal method is not limited thereto. The supernatant can be used as an extract of cells or tissues.

The extracts of cells or tissues of the present invention prepared by methods comprising the step of immersing cells or tissues in a solvent include, for example, skin extract and peripheral blood mononuclear cell extract (peripheral blood extract), but are not limited thereto.

The peripheral blood extract is prepared by the following method: after collecting blood with a syringe or the like, the cells are frozen in a freezer or liquid nitrogen, on dry ice, or such, and then thawed at a temperature of 0° C. or higher. Then, to remove insoluble cellular components, the sample is centrifuged, for example, at a gravity of 10 to 100,000 G (for example, at 440 G) and 4° C. to 25° C. (for example, at 4° C.), and the resulting supernatant is collected. The insoluble cellular components can be removed from the solvent by the method described above. However, methods for removing insoluble cellular components are not limited to the above example. The resulting supernatant can be used as an extract of cells or tissues. Alternatively, instead of centrifugation, insoluble cellular components can be removed by filtration through a nitrocellulose filter with micro pores of 0.45 μm, or the like. Alternatively, collected peripheral blood may be allowed to stand for three to 48 hours at 4° C. to induce cell necrosis. The intracellular components can be released from peripheral blood cells by this treatment. Then, to remove insoluble cellular components from the solvent, the sample is centrifuged at a gravity of 10 to 100,000 G (for example, at 440 G), and the resulting supernatant is collected. The insoluble cellular components can be removed from the solvent by the method described above, but are not limited thereto. The resulting supernatant can be used as an extract of cells or tissues. Alternatively, instead of centrifugation, insoluble cellular components can be removed by filtration through a nitrocellulose filter with micro pores of 0.45 μm of the like.

Meanwhile, cell extracts are prepared from peripheral blood mononuclear cells by the following method: peripheral whole blood is collected using a syringe or the like, and then the whole sample is diluted up to 4 ml with PBS. After 3 ml of Ficoll-Paque Plus (GE) is placed into a centrifuge tube, the diluted blood is overlaid onto the Ficoll layer. The tube is centrifuged at 400 G and 18° C. for 40 minutes. The resulting middle layer containing mononuclear cells is transferred into a fresh centrifuge tube, and 45 ml of PBS is added thereto. The sample is centrifuged at 800 G and 18° C. for five minutes, and the resulting supernatant is removed. 45 ml of PBS is added to the cells again, and the sample is centrifuged at 800 G and 18° C. for five minutes. The resulting supernatant is removed. 200 μl of PBS is added to the precipitated cells and suspended. The cell suspension is allowed to stand at −80° C. in a freezer for 30 minutes. The frozen suspension is taken out of the freezer and thawed on ice. The freeze-thaw treatment is repeated three times. Then, the sample is centrifuged at 800 G and 4° C. for 15 minutes, and the supernatant is collected. Alternatively, instead of freezing the cells, the cell sample may be allowed to stand at 4° C. for three to 48 hours to induce cell necrosis. The intracellular components can be released by this treatment. Alternatively, the cells may be disrupted by sonication with cooling on ice. The intracellular components can be released by this treatment. In either case, after releasing the intracellular components to the outside of the cells, the sample is centrifuged at a gravity of 440 to 1,000,000 preferably 20,000 to 100,000 G. The resulting supernatant is collected as a cell extract. Alternatively, instead of centrifugation, insoluble components can be removed by filtration through a nitrocellulose or cellulose acetate filter with micro pores of 0.45 μm, or the like. The resulting filtrate is used as a cell extract.

Further, the present invention relates to pharmaceutical agents to be administered to blood vessel or muscle for use in mobilizing bone marrow cells to peripheral blood from bone marrow, comprising a heparin-binding fraction produced by a method that comprises the following steps:
(a) immersing the cells or tissue in a solvent;
(b) contacting an extract obtained by the step (a) with immobilized heparin; and
(c) eluting a heparin-binding fraction (may also be expressed as heparin-purified fraction or heparin-column purified fraction) from the immobilized heparin.

"Immobilized heparin" refers to heparin covalently bound to an insoluble carrier. Examples of the insoluble carrier include, but are not limited to, Sepharose beads (such as Sepharose 4B, Sepharose 6B and such: GE Healthcare). In the present invention, a commercially available immobilized heparin (Hitrap Heparin HP column: GE Healthcare) may also be used.

Examples of conditions for contacting an extract of cells or tissues with immobilized heparin include, but are not limited to, about pH 7 to 8 (preferably pH 7.5), and a salt concentration of 0 to 200 mM, and preferably about 100 to 200 mM. The time the extract is in contact with immobilized heparin is not specifically limited, but the contact is preferably retained for 5 minutes or more in view of sufficient adsorption of the heparin-binding fraction onto immobilized heparin. Examples of the temperature include, but are not limited to, 4 to 8° C., and preferably 4° C. Further, examples of the elution condition of the heparin-binding fraction adsorbed onto the immobilized heparin include, but are not limited to, a pH of about 7 to 8 and a salt concentration of 200 to 1,000 mM (preferably about 1,000 mM).

When administered to blood vessel or muscle, pharmaceutical agents containing the extract or fraction described above mobilize bone marrow tissue stem cells into the peripheral blood circulation and can promote the regeneration of damaged tissues. Furthermore, the above-described pharmaceutical agents are expected to be used not only as an inducer/promoter for functional tissue regeneration, but also as a so-called preventive drug to prevent the functional impairment of tissues/organs caused by reduction in the number of tissue stem cells or as an anti-aging drug to delay the progress of age-related changes.

Alternatively, such treatment can be achieved by administering the agent described above; collecting and concentrating the pluripotent stem cells mobilized to peripheral blood outside the body, and then administering the cells to lesion sites. Conventional therapy using bone marrow mesenchymal stem cells is invasive because cells are collected from the bone marrow located deeply inside the body. Meanwhile, by using the agents of the present invention, bone marrow mesenchymal stem cells can be collected from peripheral blood in a less invasive manner and used for bone marrow mesenchymal stem cell transplantation or such.

The present invention also provides kits for mobilizing a bone marrow cell to peripheral blood from bone marrow, which consists of compositions to be administered to blood vessel or muscle and which comprise the materials of any one of:
(a) an HMGB1 protein;
(b) a cell that secretes an HMGB1 protein;
(c) a vector inserted with a DNA encoding an HMGB1 protein;
(d) an HMGB2 protein;
(e) a cell that secretes an HMGB2 protein;
(f) a vector inserted with a DNA encoding an HMGB2 protein;
(g) an HMGB3 protein;
(h) a cell that secretes an HMGB3 protein; and
(i) a vector inserted with a DNA encoding an HMGB3 protein.

Furthermore, the present invention provides kits for mobilizing bone marrow cells to peripheral blood from bone marrow, which comprise extracts of cells or tissues produced by a method comprising the step of immersing cells or tissues in a solvent and which are to be administered to blood vessel or muscle.

The present invention also provides kits for mobilizing bone marrow cells to peripheral blood from bone marrow, which comprise a heparin-binding fraction to be administered to blood vessel or muscle and which is produced by a method comprising the steps of:
(a) immersing a cell or tissue in a solvent;
(b) contacting immobilized heparin with the extract prepared in step (a); and
(c) eluting a heparin-binding fraction from the immobilized heparin.

The above-described kits for mobilizing bone marrow cells to peripheral blood are characterized in that administration to blood vessel or muscle mobilizes bone marrow tissue stem cells into peripheral blood circulation.

Examples of the above-described kits include: kits for promoting tissue regeneration comprising (1) the above-mentioned extract or the above-mentioned fraction or such dissolved in fibrinogen, and (2) thrombin; or alternatively, kits for promoting tissue regeneration comprising (1) the above-mentioned extract or the above-mentioned fraction or such, (2) fibrinogen, and (3) thrombin. In the present invention, commercially available fibrinogen and thrombin can be used. Examples include, but are not limited to, fibrinogen HT-Wf (Benesis-Mitsubishi Pharma), Beriplast (ZLB Behring), Tisseel (Baxter), Bolheal (Kaketsuken), and TachoComb (ZLB Behring).

Bone marrow-derived cells that are mobilized to the damaged tissue differentiate into various types of cells to contribute to functional regeneration of the damaged tissue and maintenance/enhancement of the functions. In the present invention, examples of damaged tissue include, but are not limited to, tissues damaged by various pathological conditions, trauma, burns, inflammation, autoimmunity, gene abnormalities, and the like causing ischemic/hypoperfusive/hypoxic conditions. Damaged tissue also includes necrosed tissues.

Tissues in the present invention are not particularly limited as long as bone marrow-derived cells can differentiate into the tissues. All types of tissues in the living body can be exemplified, such as skin tissue, bone tissue, cartilage tissue, muscle tissue, adipose tissue, cardiac muscle tissue, neurological tissue, pulmonary tissue, gastrointestinal tissues, hepatic/biliary/pancreatic tissues, and genitourinary organs. Moreover, with use of the above tissue regeneration promoters, treatments for inducing functional tissue regeneration becomes possible not only in cutaneous diseases such as intractable cutaneous ulcers, skin wounds, bullosis, and alopecia, but also in tissue damages such as cerebral infarction, myocardial infarction, bone fracture, pulmonary infarction, gastric ulcers, and enteritis. The types of animals to be administered with the above tissue regeneration promoters include human and non-human animals, which can be exemplified by, but are not limited to, humans, mice, rats, monkeys, pigs, dogs, rabbits, hamsters, and guinea pigs.

Bone marrow cells of the present invention are cells other than hematopoietic stem cells, or cells derived therefrom such as leukocytes, erythrocytes, and platelets, and include stem cells represented by cells which have been hitherto called bone marrow mesenchymal stem cells, bone marrow stromal pluripotent stem cells, or bone marrow pluripotent stem cells and tissue progenitor cell populations existing in the bone marrow. Bone marrow cells of the present invention can be isolated from bone-marrow extracts (bone marrow cell extracts) or peripheral blood collection. Hematopoietic stem cells are nonadherent, while bone marrow cells of the present invention are obtained as adherent cells by means of a cell culture of a mononuclear cell fraction of blood obtained from the bone marrow extracts (bone marrow cell extracts) or peripheral blood collection. Moreover, bone marrow cells of the present invention include mesenchymal stem cells, and have a potential to differentiate into, preferably, osteoblasts (the induction of differentiation can be identified by observing calcification), chondrocytes (which can be identified by alcian blue positive staining, safranin O positive staining, or the like), adipocytes (which can be identified by Sudan III positive staining), and other mesenchymal cells such as fibroblasts, smooth muscle cells, stromal cells, and tendon cells; and further nerve cells, epithelial cells (for example, epidermal keratinocytes and intestinal epithelial cells express cytokeratin family), and vascular endothelial cells. However, the cells to be differentiated into are not limited to the above cells, and the potential to differentiate into cells of parenchymatous organs such as liver, kidney, and pancreas are also included.

In the present invention, bone marrow-derived mesenchymal stem cells, bone marrow stromal pluripotent stem cells, or bone marrow pluripotent stem cells refer to cells existing in the bone marrow, which are directly collected from the bone marrow or indirectly collected from other tissues (blood, skin, adipose, and other tissues), and can be cultured/proliferated as adherent cells on a culture dish (made of plastic or glass). These cells are characterized in having a potential to differentiate into mesenchymal tissues (mesenchymal stem cells) such as bone, cartilage, and adipose, or skeletal muscles, heart muscles, further, nerve tissues, epithelial tissues (pluripotent stem cells) and can be obtained from a collection of bone marrow blood, peripheral blood, or mesenchymal tissues such as adipose, epithelial tissues such as skin, nerve tissues such as brain. Bone marrow-derived mesenchymal stem cells, bone marrow-derived pluripotent stem cells, or bone marrow pluripotent stem cells are also characterized in having a potential to differentiate into epithelial tissues such as keratinocytes that constitute skin or into nerve tissues that constitute brain, by administrating these cells that have once adhered onto a culture dish to a lesion area of the living body.

Bone marrow mesenchymal stem cells, bone marrow stromal pluripotent stem cells, or bone marrow pluripotent stem cells of the present invention are multipotent stem cells, and have a potency to differentiate preferably into: osteoblasts (the induction of differentiation can be identified by observing calcification), chondrocytes (which can be identified by alcian blue positive staining, safranin O positive staining, or the like), adipocytes (which can be identified by Sudan III positive staining or the like), and other mesenchymal cells such as fibroblasts, smooth muscle cells, skeletal muscle cells, stromal cells, and tendon cells; nerve cells, pigment cells, epidermal cells, hair follicle cells (which express cytokeratin family, hair keratin family, or the like), epithelial cells (for example, epidermal keratinocytes and intestinal epithelial cells express cytokeratin family or the like), and endothelial cells; and further preferably into cells of parenchymatous organs such as liver, kidney, and pancreas. However, differentiated cells are not limited to the above cells.

Moreover, human bone marrow mesenchymal stem cells, bone marrow stromal pluripotent stem cells, or bone marrow pluripotent stem cells can be exemplified by, but are not limited to, cells which can be directly obtained from collecting bone marrow (bone marrow cell extracts), peripheral blood, or adipose, or obtained as adherent cells through culturing of an isolated mononuclear cell fraction. Markers for human bone marrow mesenchymal stem cells, bone marrow stromal pluripotent stem cells, or bone marrow pluripotent stem cells can be, for example, all or some of the markers of Lin-negative, CD45-negative, and CD44-positive, but are not limited to.

Moreover, mouse bone marrow mesenchymal stem cells, bone marrow stromal pluripotent stem cells, or bone marrow pluripotent stem cells can be exemplified by, but are not limited to, cells which can be obtained by methods described in the Examples. Markers for mouse bone marrow mesenchymal stem cells, bone marrow stromal pluripotent stem cells, or bone marrow pluripotent stem cells can be for example, all or some of the markers of CD44-positive, PDGFRα-positive, PDGFRβ-positive, CD45-negative, Lin-negative, Sca-1 positive, and c-kit negative, but are not limited to.

Tissue progenitor cells are defined as undifferentiated cells having a unidirectional potency to differentiate into specific tissue cells other than the blood system, and include undifferentiated cells having the potency to differentiate into mesenchymal tissue, epithelial tissue, nerve tissue, parenchymatous organs, and vascular endothelium as mentioned above.

For pharmaceutical agents of the present invention, there is no particular limitation in components other than the extract, the heparin-binding fraction, and at least one of the ingredients (a) to (i) mentioned above, so long as the component does not inhibit the bone marrow cell mobilization and the promotion of tissue regeneration. For example, in addition to the extract, the heparin-binding fraction, and at least one of the substances (a) to (i) mentioned above, the pharmaceutical agents of the present invention may contain: molecules (molecular groups) related to the enhancement of the function of HMGB1, HMGB2, or HMGB3 to induce functional tissue regeneration; molecules (molecular groups) which inhibit unanticipated actions of HMGB1, HMGB2, or HMGB3; factors which regulate proliferation and differentiation of bone marrow cells; and other factors which enhance/maintain these factors or cellular functions.

The types of animals which serve as a source of an extract, a heparin-binding fraction or HMGB1, HMGB2, or HMGB3 protein for the pharmaceutical agents of the present invention include human and non-human animals, which can be exemplified by humans, mice, rats, monkeys, pigs, dogs, rabbits, hamsters, and guinea pigs, but the type of animal is preferably the same as the animal to be administered with the extract and the like.

The HMGB1 protein in pharmaceutical agents of the present invention can be exemplified by, but is not limited to proteins comprising the amino acid sequence of SEQ ID NO: 1, 3, or 5. HMGB1 proteins of the present invention can also include proteins which are functionally equivalent to the protein comprising the amino acid sequence of SEQ ID NO: 1, 3, or 5. Examples of such proteins include: 1) isolated proteins which comprise an amino acid sequence with one or more amino acid substitutions, deletions, insertions, and/or additions in the amino acid sequence of SEQ ID NO: 1, 3, or 5, and which are functionally equivalent to the protein comprising the amino acid sequence of SEQ ID NO: 1, 3, or 5; and 2) isolated proteins which are encoded by DNAs that hybridize under stringent conditions with DNAs comprising the nucleotide sequence of SEQ ID NO: 2, 4, or 6, and which are functionally equivalent to the protein comprising the amino acid sequence of SEQ ID NO: 1, 3, or 5.

The HMGB2 protein in pharmaceutical agents of the present invention can be exemplified by, but is not limited to proteins comprising the amino acid sequence of SEQ ID NO: 7, 9, or 11. HMGB2 proteins of the present invention can also include proteins which are functionally equivalent to the protein comprising the amino acid sequence of SEQ ID NO: 7, 9, or 11. Examples of such proteins include: 1) isolated proteins which comprise an amino acid sequence with one or more amino acid substitutions, deletions, insertions, and/or additions in the amino acid sequence of SEQ ID NO: 7, 9, or 11, and which are functionally equivalent to the protein comprising the amino acid sequence of SEQ ID NO: 7, 9, or 11; and 2) isolated proteins which are encoded by DNAs that hybridize under stringent conditions with DNAs comprising the nucleotide sequence of SEQ ID NO: 8, 10, or 12, and which are functionally equivalent to the protein comprising the amino acid sequence of SEQ ID NO: 7, 9, or 11.

The HMGB3 protein in pharmaceutical agents of the present invention can be exemplified by, but is not limited to proteins comprising the amino acid sequence of SEQ ID NO: 13 or 15. HMGB3 proteins of the present invention can also include proteins which are functionally equivalent to the protein comprising the amino acid sequence of SEQ ID NO: 13 or 15. Examples of such proteins include: 1) isolated proteins which comprise an amino acid sequence with one or more amino acid substitutions, deletions, insertions, and/or additions in the amino acid sequence of SEQ ID NO: 13 or 15, and which are functionally equivalent to the protein comprising the amino acid sequence of SEQ ID NO: 13 or 15; and 2) isolated proteins which are encoded by DNAs that hybridize under stringent conditions with DNAs comprising the nucleotide sequence of SEQ ID NO: 14 or 16, and which are functionally equivalent to the protein comprising the amino acid sequence of SEQ ID NO: 13 or 15.

Isolated proteins which are functionally equivalent to the protein comprising the amino acid sequence of SEQ ID NO: 1, 3, 5, 7, 9, 11, 13, or 15 may be homologues or paralogues to the protein comprising the amino acid sequence of SEQ ID NO: 1, 3, 5, 7, 9, 11, 13, or 15. Those skilled in the art can isolate proteins which are functionally equivalent to the protein comprising the amino acid sequence of SEQ ID NO: 1, 3, 5, 7, 9, 11, 13, or 15, by known methods (supplementary volume of "Jikken Igaku (Experimental Medicine), Idenshi Kougaku Handbook (Genetic Engineering Handbook)", pp. 246-251, published by Yodosha Co., Ltd., 1991).

Examples of proteins which are functionally equivalent to the protein comprising the amino acid sequence of SEQ ID NO: 1, 3, 5, 7, 9, 11, 13, or 15 include proteins having bone marrow-derived cell-inducing activity.

Proteins which comprise an amino acid sequence with one or more amino acid substitutions, deletions, insertions, and/or additions in the amino acid sequence of SEQ ID NO: 1, 3, 5, 7, 9, 11, 13, or 15, and which are functionally equivalent to the protein comprising the amino acid sequence of SEQ ID NO: 1, 3, 5, 7, 9, 11, 13, or 15 include naturally-occurring proteins. Generally, eukaryotic genes have polymorphism as known in interferon genes and such. Alterations in nucleotide sequence caused by the polymorphism may result in one or more amino acid substitutions, deletions, insertions, and/or additions. Naturally-occurring proteins such as those comprising an amino acid sequence with one or more amino acid substitutions, deletions, insertions, and/or additions in the amino acid sequence of SEQ ID NO: 1, 3, 5, 7, 9, 11, 13, or 15, and which are functionally equivalent to the protein comprising the amino acid sequence of SEQ ID NO: 1, 3, 5, 7, 9, 11, 13, or 15 are included in HMGB1, HMGB2, or HMGB3 proteins of the present invention.

The present invention also includes artificially-produced mutant proteins as long as they are functionally equivalent to the protein comprising the amino acid sequence of SEQ ID NO: 1, 3, 5, 7, 9, 11, 13, or 15. Known methods which cause random mutations to a given nucleotide sequence include substitution(s) of base pair(s) through nitrous acid treatment of DNA (Hirose, S. et al., Proc. Natl. Acad. Sci. USA., 79: 7258-7260, 1982). This method enables random introduction of substitution(s) of base pair(s) into a specific segment by nitrous acid treatment of the segment desired to be mutated. Alternatively, technologies for site-directing a target mutation include the gapped duplex method (Kramer W. and Fritz H J., Methods in Enzymol., 154: 350-367, 1987) and the like. A cyclic double stranded vector in which a gene to be introduced with a mutation is cloned is separated into single strands. These single strands are hybridized with a synthetic oligonucleotide mutated at the target site. A vector-derived complementary single strand DNA linearized by a restriction enzyme is annealed with the cyclic single stranded vector, and the gap between the oligonucleotide and the vector is filled by using a DNA polymerase, which is then made into a complete double-stranded vector by ligation.

The number of amino acids to be modified would be typically within 50, preferably within 30, and more preferably within 5 amino acids (for example, one amino acid).

When an amino acid is artificially substituted, substitution with an amino acid having similar properties would result in maintaining the activity of the original protein. Proteins of the present invention include proteins resulting from a conservative substitution in the above substitution of amino acid(s), and which are functionally equivalent to the protein comprising the amino acid sequence of SEQ ID NO: 1, 3, 5, 7, 9, 11, 13, or 15. Conservative substitution is considered important when substituting amino acid(s) of domains important for protein activities. Such a conservative substitution of amino acid(s) is well known to those skilled in the art.

Examples of amino acid groups suitable for conservative substitution include basic amino acids (such as lysine, arginine, and histidine), acidic amino acids (such as aspartic acid and glutamic acid), uncharged polar amino acids (such as glycine, asparagine, glutamine, serine, threonine, tyrosine, and cysteine), nonpolar amino acids (such as alanine, valine, leucine, isoleucine, proline, phenylalanine, methionine, and tryptophane), β branched amino acids (such as threonine, valine, and isoleucine), and aromatic amino acids (such as tyrosine, phenylalanine, tryptophane, and histidine).

Moreover, non-conservative substitution may increase protein activities (for example, constitutively activated proteins).

In addition, proteins which are functionally equivalent to the protein comprising the amino acid sequence of SEQ ID NO: 1, 3, 5, 7, 9, 11, 13, or 15 can be obtained by methods that utilize hybridization. That is to say, a DNA encoding HMGB1, HMGB2, or HMGB3 protein of the present invention as shown in the SEQ ID NO: 2, 4, 6, 8, 10, 12, 14, or 16, or a fragment thereof is used as a probe, and then DNAs that can hybridize to them are isolated. A hybridization reaction performed under stringent conditions leads to the selection of highly homologous DNA as a nucleotide sequence. This increases the chances of isolated proteins containing proteins that are functionally equivalent to the HMGB1, HMGB2, or HMGB3 protein. Examples of a highly homologous nucleotide sequence include those having 70% or more, and desirably 90% or more identity.

In a specific example, the term "stringent conditions" refers to hybridization conditions with 6× SSC, 40% formamide at 25° C. and subsequent washing with 1×SSC at 55° C. The stringency depends on conditions such as salt concentration, formamide concentration, or temperature; however, it is obvious for those skilled in the art to set these conditions so as to obtain necessary stringency.

With the use of hybridization, for example, DNAs encoding homologues of the HMGB1, HMGB2, or HMGB3 proteins other than those proteins comprising the amino acid sequence of SEQ ID NO: 1, 3, 5, 7, 9, 11, 13, or 15 can be isolated.

Proteins which are functionally equivalent to a protein comprising the amino acid sequence of SEQ ID NO: 1, 3, 5, 7, 9, 11, 13, or 15 normally have a high homology with the amino acid sequence of SEQ ID NO: 1, 3, 5, 7, 9, 11, 13, or 15. The term "high homology" refers to a sequence identity of at least 30% or more, preferably 50% or more, more preferably 80% or more (for example, 95% or more). The identity of the nucleotide sequences and amino acid sequences can be determined using a homology search site via the internet (For example, homology searches such as FASTA, BLAST, PSI-BLAST, and SSEARCH can be used in the DNA Data Bank of Japan (DDBJ) [examples of which include the homology search page (Search and Analysis) at the DNA Data Bank of Japan (DDBJ) website. Furthermore, searches using BLAST can be carried out through the web site of the National Center for Biotechnology Information (NCBI) (examples of which include BLAST page at the homepage of NCBI website; Altschul, S.F. et al., J. Mol. Biol., 1990, 215(3): 403-10; Altschul, S.F. & Gish, W., Meth. Enzymol., 1996, 266: 460-480; Altschul, S.F. et al., Nucleic Acids Res., 1997, 25: 3389-3402)).

For example, in the calculation of the identity of amino acid sequences using Advanced BLAST 2.1, the identity value (%) can be obtained by the following: blastp is used as the program, expect value is set at 10, all filters are set at OFF, BLOSUM62 is used for matrix, and gap existence cost, per residue gap cost, and lambda ratio are set at 11, 1, and 0.85, respectively (default parameters) (Karlin, S, and S. F. Altschul (1990) Proc. Natl. Acad. Sci. USA 87: 2264-68; Karlin, S, and S. F. Altschul (1993) Proc. Natl. Acad. Sci. USA 90: 5873-7).

Proteins of the present invention, or proteins functionally equivalent thereto may be proteins subjected to various modifications such as physiological modification with sugar chains and the like, labeling with fluorescence or radioactive substances, or fusion with other proteins. Particularly in recombinants that will be described later, sugar chain modification may vary depending on the hosts used for expression. However, even if there is a difference in sugar chain modifications, all proteins having properties similar to those of HMGB1, HMGB2, or HMGB3 proteins disclosed herein are HMGB1, HMGB2, or HMGB3 proteins of the present invention or proteins functionally equivalent thereto.

HMGB1, HMGB2, or HMGB3 proteins can be obtained not only from living materials, but also in the form of recombinants by incorporating genes that encode these proteins into an appropriate expression system. In order to obtain HMGB1, HMGB2, or HMGB3 proteins by genetic engineering techniques, the above-mentioned DNAs which encode HMGB1, HMGB2, or HMGB3 proteins may be incorporated into an appropriate expression system, and they can then be expressed. Examples of host/vector systems applicable to the present invention include the expression vector pGEX and *E. coli*. With pGEX, foreign genes can be expressed as a fusion protein with glutathione-S-transferase (GST) (Gene, 67: 31-40, 1988). pGEX incorporated with a gene encoding the HMGB1, HMGB2, or HMGB3 protein is introduced into an *E. coli* strain such as BL21 by heat shock, incubated for an appropriate time and then isopropylthio-β-D-galactoside (IPTG) is added to induce the expression of GST-fused HMGB1, GST-fused HMGB2, or GST-fused HMGB3 proteins. Since GST of the present invention adsorbs onto Glutathione Sepharose 4B, the expression product is readily separated and purified by affinity column chromatography.

In addition, the following may also be applied as host/vector systems to obtain recombinants of HMGB1, HMGB2, or HMGB3 proteins. First, when bacteria are used as hosts, expression vectors for fusion proteins that utilize histidine-tag, HA-tag, FLAG-tag, and the like are commercially available. Regarding yeasts, yeasts belonging to the genus *Pichia* are known to be effective for the expression of sugar chain-containing proteins. In terms of the addition of sugar chains, expression systems that utilize baculovirus vector with insect cells as a host are also useful (Bio/Technology, 6: 47-55, 1988). Further, using mammalian cells, transfection of a vector is carried out using promoters such as CMV, RSV, and SV40. Any of these host/vector systems can be used as an expression system of HMGB1, HMGB2, or HMGB3 proteins. Moreover, genes can also be introduced using viral vectors such as retrovirus vectors, adenovirus vectors, and adeno-associated virus vectors.

Thus obtained proteins of the present invention may be isolated intracellularly or extracellularly (medium and such), and can be purified as proteins that are substantially pure and homogenous. Proteins may be separated and purified using separation and purification methods which are commonly used in protein purification, and are not particularly limited. For example, proteins can be separated and purified by appropriately selecting and combining a chromatography columns, filters, ultrafiltration, salting out, solvent precipitation, solvent extraction, distillation, immunoprecipitation, SDS-polyacrylamide gel electrophoresis, isoelectric focusing electrophoresis, dialysis, recrystallization, and the like.

Examples of chromatographies include affinity chromatography, ion-exchange chromatography, hydrophobic chromatography, gel filtration, reverse phase chromatography, and adsorption chromatography (Marshak et al., Strategies for Protein Purification and Characterization: A Laboratory Course Manual. Ed Daniel R. Cold Spring Harbor Laboratory Press, 1996). These chromatographies can be performed using liquid phase chromatographies such as HPLC and FPLC.

Moreover, proteins of the present invention are preferably substantially purified proteins. Here, the term "substantially purified" means that the protein purity of the present invention (proportion of the protein of the present invention in total protein components) is 50% or more, 60% or more, 70% or more, 80% or more, 90% or more, 95% or more, 100% or close to 100%. The upper limit for "close to 100%" depends on the purification techniques and analytical techniques of those skilled in the art, of which examples are 99.999%, 99.99%, 99.9%, 99%, and the like.

Moreover, a substantially purified protein includes any protein purified by any purification method as long as the protein purity is as mentioned above. Examples include, but are not limited to, proteins substantially purified by appropriately selecting and combining the above-mentioned chromatography columns, filters, ultrafiltration, salting out, solvent precipitation, solvent extraction, distillation, immunoprecipitation, SDS-polyacrylamide gel electrophoresis, isoelectric focusing electrophoresis, dialysis, recrystallization, and the like.

Cells where HMGB1, HMGB2, or HMGB3 proteins of the pharmaceutical agents of the present invention are released or secreted basically include all types of tissue-derived cells in vivo. Cells which can be readily collected and cultured are exemplified by, but are not limited to, fibroblasts (such as normal skin fibroblasts and cell lines derived therefrom). Moreover, cells secreting HMGB1, HMGB2, or HMGB3 proteins can also be produced by the following manner. A vector is produced by inserting an HMGB1, HMGB2, or HMGB3 protein-encoding DNA, or an HMGB1, HMGB2, or HMGB3 protein-encoding DNA linked with a secretion signal-encoding DNA (ATG CAG ACA GAC ACA CTC CTG CTA TGG GTA CTG CTG CTG TGG GTT CCA GGT TCC ACT GGT GAC; SEQ ID NO: 17), into a known expression vector or a gene therapy vector. The produced vector is introduced into mammalian cells such as fibroblasts (such as normal skin fibroblasts and cell lines derived therefrom), insect cells, and other cells. Examples of secretion signal-encoding DNAs include, but are not limited to, DNAs with the above-described sequences. There are no particular limitations in the animal type from which these cells derive, although cells from the animal type of the target animal subjected to tissue regeneration, cells from the target itself, or cells derived from a blood relative of the target subjected to tissue regeneration are preferably used.

DNAs which encode HMGB1, HMGB2, or HMGB3 proteins of the pharmaceutical agents of the present invention may be cDNAs, genomic DNAs, natural DNAs, or artificially-synthesized DNAs as long as they encode the HMGB1, HMGB2, or HMGB3 protein. DNAs which encode HMGB1, HMGB2, or HMGB3 proteins are normally contained in the pharmaceutical agents of the present invention in a form inserted in vectors (such as gene therapy vectors).

Examples of the gene therapy vectors of the present invention include, but are not limited to, plasmid vectors, retrovirus vectors, lentivirus vectors, adenovirus vectors, adeno-associated virus vectors, Sendai virus vectors, Sendai virus envelope vectors, and papilloma virus vectors. The gene therapy vectors may contain promoter DNA sequences which effectively induce gene expression, factors that regulate gene expression, and molecules which are necessary for maintaining DNA stability.

Pharmaceutical agents of the present invention may also contain: partial peptides of HMGB1, HMGB2, or HMGB3 protein which have an activity of mobilizing bone marrow cells to peripheral blood from bone marrow; cells secreting these partial peptides; or vectors inserted with the DNAs encoding these partial peptides.

Methods for administering pharmaceutical agents of the present invention are parenteral administration into blood vessel or muscle. Specific examples of the administration methods include administration by injection. For example, pharmaceutical agents of the present invention can be administered into blood vessel or muscle by intravascular injection (intraarterial injection, intravenous injection, or such), or intramuscular injection.

The method of administration may be appropriately selected according to the age and the symptoms of the patient. When an HMGB1, HMGB2, or HMGB3 protein is administered, the dose of the protein per use can be selected within a range of 0.0000001 mg to 1,000 mg per kg body weight of a patient. Alternatively, the dose can be selected within a range of 0.00001 mg to 100,000 mg per body of patient, for example. When administering cells secreting HMGB1, HMGB2, or HMGB3 proteins or gene therapy vectors inserted with DNAs encoding HMGB1, HMGB2, or HMGB3 proteins they may be administered such that the amounts of HMGB1, HMGB2, or HMGB3 protein are within the above range. However, the dosage of the pharmaceutical agents of the present invention is not limited thereto.

Pharmaceutical agents of the present invention can be formulated according to the usual methods (for example, Remington's Pharmaceutical Science, latest edition, Mark Publishing Company, Easton, U.S.A), and may contain pharmaceutically acceptable carriers and additives together. Examples include surfactants, excipients, colorants, perfumes, preservatives, stabilizers, buffers, suspending agents, isotonizing agents, binders, disintegrants, lubricants, flow promoters, and flavoring agents, although they are not limited thereto and other common carriers may be appropriately used. Specific examples include light anhydrous silicic acid, lactose, crystalline cellulose, mannitol, starch, carmellose calcium, carmellose sodium, hydroxypropylcellulose, hydroxypropylmethylcellulose, polyvinylacetaldiethylamino acetate, polyvinylpyrrolidone, gelatin, medium-chain fatty acid triglyceride, polyoxyethylene hydrogenated castor oil 60, white sugar, carboxymethyl cellulose, corn starch, and inorganic salts.

Moreover, applications of the above-mentioned extracts of cells or tissues, heparin-binding fractions, HMGB1, HMGB2, or HMGB3 proteins, cells secreting HMGB1, HMGB2, or HMGB3 proteins, vectors inserted with DNAs encoding HMGB1, HMGB2, or HMGB3 proteins, partial peptides of HMGB1, HMGB2, or HMGB3 proteins, cells secreting these partial peptides; or vectors inserted with DNAs encoding these partial peptides can be expressed as (1) to (3) below:

(1) methods for mobilizing bone marrow cells to peripheral blood from bone marrow, which comprise the step of administering to blood vessel or muscle, extracts of cells or tissues, heparin-binding fractions, HMGB1, HMGB2, and HMGB3 proteins, cells that secrete the proteins, vectors inserted with DNAs encoding the proteins, partial peptides of the proteins, cells that secrete the partial peptides, or vectors inserted with DNAs encoding the partial peptides;

(2) uses of extracts of cells or tissues, heparin-binding fractions, HMGB1, HMGB2, and HMGB3 proteins, cells that secrete the proteins, vectors inserted with DNAs encoding the proteins, partial peptides of the proteins, cells that secrete the partial peptides, or vectors inserted with DNAs encoding the partial peptides, in the preparation of pharmaceutical agents administered to blood vessel or muscle for mobilizing bone marrow cells to peripheral blood from bone marrow; and (3) extracts of cells or tissues, heparin-binding fractions, HMGB1, HMGB2, and HMGB3 proteins, cells that secrete the proteins, vectors inserted with DNAs encoding the proteins, partial peptides of the proteins, cells that secrete the partial peptides, and vectors inserted with DNAs encoding the partial peptides, for use in methods for mobilizing bone marrow cells to peripheral blood from bone marrow, which are administered to blood vessel or muscle.

The present invention also provides methods for assessing whether or not factors that mobilize bone marrow cells to peripheral blood from bone marrow are contained in extracts of cells or tissues, in which the method comprises the following steps:

(a) preparing extracts of cells or tissues; and
(b) measuring the activity of mobilizing bone marrow cells to peripheral blood from bone marrow prepared in step (a).

If the activity of mobilizing bone marrow cells to peripheral blood from bone marrow in step (b) is higher than that of the control, the method can also be used to determine that the extracts of cells or tissues contains the factors that mobilize bone marrow cells to peripheral blood from bone marrow.

In the above method, first, cells or tissue are immersed in a solvent. These cells are not specifically limited, and examples include tissue-derived cells and cell lines established from tissue-derived cells (such as HeLa and HEK293, without being limited thereto), isolated cells, non-isolated cells (such as cells existing in isolated tissues), cells introduced with a DNA encoding an HMGB1, HMGB2, or HMGB3 protein. Any tissue may be applied as the tissue described as above and examples include, without limitation, living skin tissues, tissues for internal biopsy (operation) (such as brain, lung, heart, liver, stomach, small intestine, large intestine, pancreas, kidney, bladder, spleen, uterus, testis, and blood), and damaged tissues. Moreover, examples of the solvent include, but are not limited to, physiological saline, PBS and TBS. Further, the time for immersing cells or tissue in a solvent is preferably a time necessary and sufficient for inducing cellular necrosis, (normally 24 hours or more), without being limited thereto. Moreover, in the present invention, cells or tissue are immersed in a solvent, and then the cells or tissue can be removed from the solvent containing the cells or tissue. The method for removing cells or tissue from the solvent is not specifically limited as long as the method is known to those skilled in the art.

Next, an activity of mobilizing bone marrow cells to peripheral blood from bone marrow by the obtained extracts of cells or tissue is measured. The control includes, for example, the solvent before immersing cells or tissues in it. The activity of mobilizing bone marrow cells can be measured, for example, by the methods described in the Examples; however, the methods are not limited thereto.

The activity of mobilizing bone marrow cells into peripheral blood circulation from bone marrow can be assayed as follows. A prepared extract of cells or tissues is administered intravenously, percutaneously, intramuscularly, or intraperitoneally; one minute to four weeks after administration, preferably one hour to 24 hours after administration, and more preferably 12 hours after administration, the peripheral blood is collected and the mononuclear cell population in the peripheral blood is assessed by flow cytometry to measure PDGFRα and CD44 double-positive cells, or PDGFRβ and CD44 double-positive cells. The activity assay method is not limited to this example.

The present invention also provides methods of screening for extracts of cells or tissues including factors that mobilize bone marrow cells to peripheral blood from bone marrow, which comprises the steps of:
(a) assaying a number of extracts by the above-described method to assess whether the extracts contain factors that mobilize bone marrow cells to peripheral blood from bone marrow; and
(b) selecting extracts that are determined in step (a) to contain factors that mobilize bone marrow cells to peripheral blood from bone marrow.

The present invention also provides methods for identifying factors that mobilize bone marrow cells to peripheral blood from bone marrow, which comprise the step of purifying the factors using the activity of mobilizing bone marrow cells as an indicator, from extracts that have been determined to contain the factors by the assessment and screening methods described above. The factors that mobilize bone marrow cells to peripheral blood from bone marrow can be purified using conventional protein isolation/purification methods. There is no limitation on the type of isolation/purification method. For example, chromatography columns, filters, ultrafiltration, salting out, solvent precipitation, solvent extraction, distillation, immunoprecipitation, SDS-polyacrylamide gel electrophoresis, isoelectric focusing electrophoresis, dialysis, recrystallization, and such may be appropriately selected and combined to isolate and purify proteins. Purified factors can be identified by methods known to those skilled in the art, for example, mass spectrometry. Identified factors can be used to mobilize bone marrow cells to peripheral blood from bone marrow. Such factors may be referred to as "candidates for mobilizing bone marrow cells to peripheral blood from bone marrow" or "candidates for contributing to the mobilization of bone marrow cells to peripheral blood from bone marrow".

All prior art documents cited herein are incorporated by reference herein.

EXAMPLES

Hereinbelow, the present invention will be specifically described with reference to the Examples, but it is not to be construed as being limited thereto.

Example 1

Purpose: Mobilization of bone marrow tissue stem cells to peripheral blood using bone marrow-derived tissue stem cell-inducing factors in skin tissue extract Methods: To achieve the above purpose, a study was conducted by the method described below.

(1) Preparation of bone marrow-derived tissue stem cell-inducer. Free skin pieces isolated from 25 neonatal mice (two days old) were immersed in 25 ml of phosphate buffered saline (PBS), pH 7.4. After 24 hours of incubation at 4° C., the sample was centrifuged at 440 G at 4° C. for ten minutes to remove the tissue. The supernatant was collected as skin extract (SE).

Meanwhile, RNA was extracted from neonatal C57/B16 mice skin using Trizol (Invitrogen), and then cDNA was synthesized using the SuperScript III cDNA Synthesis Kit (Invitrogen). Polymerase chain reaction (PCR) was carried out using this cDNA as a template to amplify HMGB1 cDNA. The HMGB1 cDNA was inserted into an mammalian cell protein expression plasmid vector, pCAGGS, to express a protein in which a Flag-tag sequence (Asp-Tyr-Lys-Asp-Asp-Asp-Lys, SEQ ID NO: 18) is attached to the N-terminus of its amino acid sequence (FIG. 1). The plasmid vector was transfected into HEK293 (cultured cell line derived from human fetal kidney cell). The cells were cultured for 48 hours to express the protein. Each sample of cells expressing the HMGB1 protein and the culture supernatant were incubated at 4° C. for 16 hours, and then centrifuged at 4,400×g for five minutes. The supernatant was collected, and anti-Flag Antibody Gel (Sigma) was added thereto in an amount of 100 µl per 50 ml of the supernatant. The mixture was incubated at 4° C. for 16 hours. The gel was collected by centrifugation, followed by five PBS washes. Then, the gel was eluted with 3× Flag peptide (final 100 µg/ml). The concentration of the eluted protein was determined using the HMGB1 ELISA Kit (Shino-Test Co.). After freeze-drying, the protein concentration was adjusted to 200 µg/ml with PBS.

Figure 2:
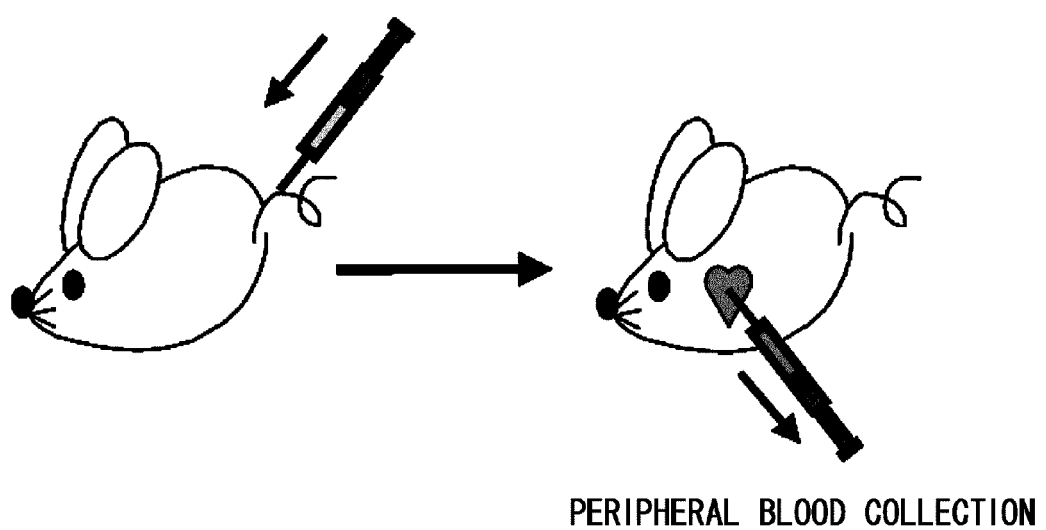
FIG. 2 presents a diagram showing administration of skin extract (SE) to a mouse via caudal vein, followed by collection of peripheral blood.

(2) Eight-week-old male mice (C57/B16) were administered with 500 µl of the above-described skin extract (SE), or 500 µl of PBS as a negative control group, via the caudal vein using syringes attached with a 30 G 1/2 injection needle (FIG. 2). Six, 12, 24, and 48 hours after administration, 1 ml of peripheral blood was collected from the hearts of the mice under inhalation anesthesia with isoflurane using a heparin-coated 1-ml syringe. The blood samples were each combined with 3 ml of PBS, and then gently overlaid onto 3 ml of Ficoll (GE healthcare). The resulting samples were centrifuged using a centrifuge at 400×g at 25° C. for 40 minutes. The cells in the opaque middle layer were collected as a mononuclear cell fraction. 1 ml of HLB solution (Immuno-Biological Laboratories Co., Ltd.), a hemolytic agent, was added to the collected cells. The cells were incubated at room temperature for five minutes. This hemolytic treatment was repeated twice. After adding 10 ml of PBS, the cells were centrifuged at 440×g at 25° C. for five minutes. The supernatants were removed, and the cells were collected. 1,000,000 cells were incubated at room temperature for 20 minutes with antibodies each diluted 100-fold with PBS including a PE-labeled anti-mouse PDGFRα antibody (e-Bioscience), PE-labeled anti-mouse PDGFRβ antibody (e-Bioscience), and PerCy5-labeled anti-mouse CD44 antibody (BD biosciences). After incubation, the cells were centrifuged at 440×g at 25° C. for five minutes. The supernatant was removed. 400 µl of PBS containing 1% paraformaldehyde was added to the cells to prepare a sample for flow cytometric analysis.

Figure 4:
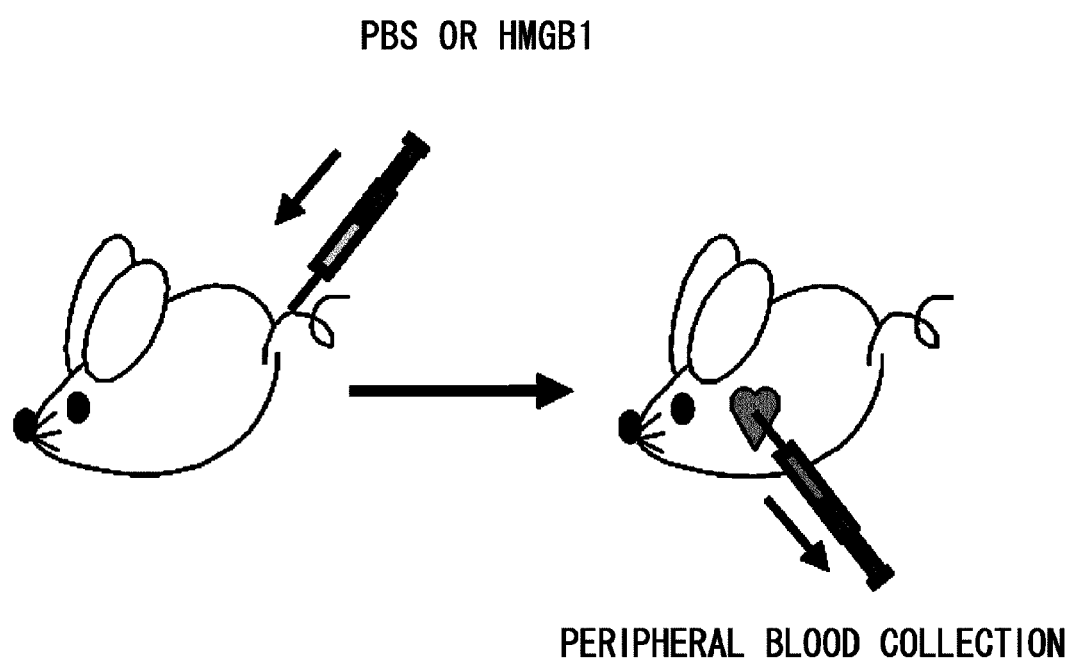
FIG. 4 shows in a diagram administration of HMGB1 to a mouse via caudal vein, followed by collection of peripheral blood.

Eight-week-old male mice (C57/B16) were administered with 250 µl of mouse HMGB1 (1 µg/µl), or 250 µl of PBS as a negative control group, via the caudal vein using syringes attached with a 30 G 1/2 injection needle (FIG. 4). 12 hours after administration, 1 ml of peripheral blood was collected from the hearts of the mice under inhalation anesthesia with isoflurane using a heparin-coated 1-ml syringe. The blood samples were each combined with 3 ml of PBS, and then gently overlaid onto 3 ml of Ficoll (GE healthcare). The resulting samples were centrifuged in a centrifuge at 400×g at 25° C. for 40 minutes. The cells in the opaque middle layer were collected as a mononuclear cell fraction. 1 ml of HLB solution (Immuno-Biological Laboratories Co., Ltd.), a hemolytic agent, was added to the collected cells. The cells were incubated at room temperature for five minutes. This hemolytic treatment was repeated twice. After adding 10 ml of PBS, the cells were centrifuged at 440×g at 25° C. for five minutes. The supernatants were removed, and the cells were collected. 1,000,000 cells were incubated at room temperature for 20 minutes with antibodies each diluted 100-fold with PBS including a PE-labeled anti-mouse PDGFRα antibody (e-Bioscience) and PerCy5-labeled anti-mouse CD44 antibody (BD biosciences). After incubation, the cells were centrifuged at 440×g at 25° C. for five minutes. The supernatant was removed. 400 µl of PBS containing 1% paraformaldehyde was added to the cells to prepare a sample for flow cytometric analysis.

Figure 3:
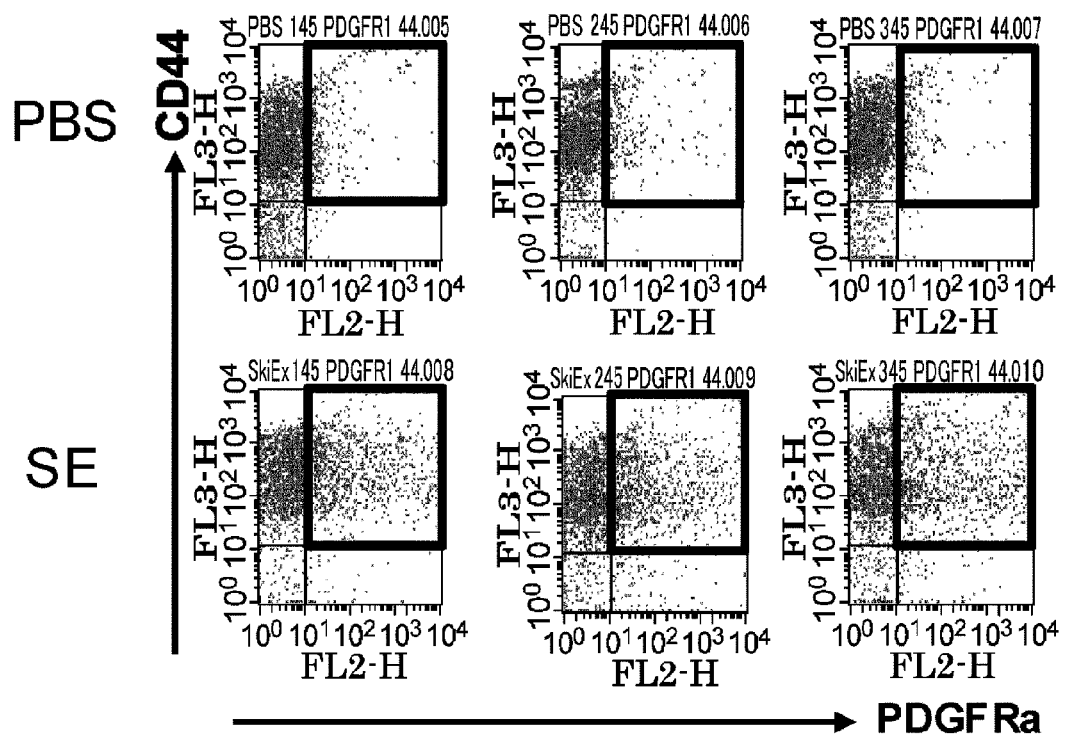
FIG. 3 shows in a diagram flow cytometric fractionation of a mouse peripheral blood mononuclear cell fraction fluorescently labeled with anti-mouse PDGFRα antibody and anti-mouse CD44 antibody 12 hours after administration of skin extract (SE). The upper three charts correspond to the PBS-administered group (n=3) as a negative control, while the lower three charts correspond to the skin extract (SE)-administered group (n=3). The vertical axis indicates the expression level of CD44, and the horizontal axis indicates the expression level of PDGFRα. The area boxed with blue line corresponds to a population of CD44 and PDGFRα double-positive cells. The population was increased in the skin extract-administered group (SE) as compared to the PBS-administered group.
Figure 5:
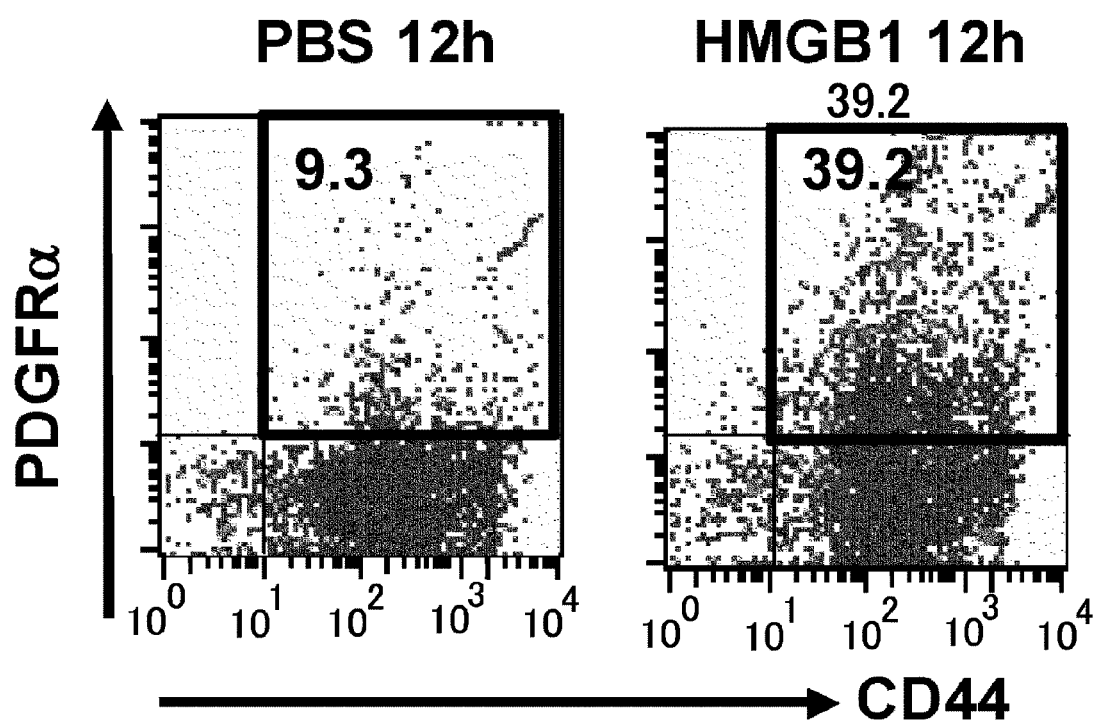
FIG. 5 shows in a diagram flow cytometric fractionation of mouse peripheral blood mononuclear cell fraction fluorescently labeled with anti-mouse PDGFRα antibody and anti-mouse CD44 antibody 12 hours after administration of HMGB1. The left chart corresponds to the PBS-administered mice as a negative control, while the right chart corresponds to the HMGB1-administered mice. The vertical axis indicates the expression level of CD44, and the horizontal axis indicates the expression level of PDGFRα. The area boxed with blue line corresponds to a population of CD44 and PDGFRα double-positive cells. The population was increased in the HMGB1-administered mice as compared to the PBS-administered mice.

Results: PDGFRα and CD44 double-positive cells were demonstrated to be significantly mobilized to peripheral blood 12 hours after injection of the skin extract (SE) (FIG. 3). Furthermore, PDGFRα and CD44 double-positive cells were demonstrated to be significantly mobilized to peripheral blood 12 hours after injection of HMGB1 (FIG. 5).

Example 2

Purpose: To test whether mesenchymal stem cells are mobilized to peripheral blood by intravenous administration of recombinant HMGB1 protein.

Methods: C57BL6 mice (eight to ten weeks old, male) were administered with 400 µl of physiological saline containing 100 µg/ml recombinant HMGB1 protein (40 µg of HMGB1) or 400 µl of physiological saline alone through the caudal vein. After 12 hours, peripheral blood was collected from the mice. The blood samples were diluted with PBS to a total volume of 4 ml. The diluted blood samples were overlaid onto 3 ml of Ficoll-Paque Plus (GE) placed in centrifuge tubes. The samples were centrifuged at 400 G at 18° C. for 40 minutes. The middle layer containing mononuclear cells was transferred to a fresh centrifuge tube, and 45 ml of PBS was added thereto. The tube was centrifuged at 800 G at 18° C. for five minutes. The supernatant was removed. Again, 45 ml of PBS was added, and the tube was centrifuged at 800 G at 18° C. for five minutes. The supernatant was removed. The prepared mononuclear cells were incubated with Phycoerythrobilin (PE)-labeled anti-mouse PDGFRα antibody and Fluorescein isothiocyanate (FITC)-labeled anti-mouse CD44 antibody. Then, the abundance of PDGFRα and CD44 double-positive cells in the mononuclear cell fraction was assessed by flow cytometry (Facscan; Becton, Dickinson and Company).

Figure 14:
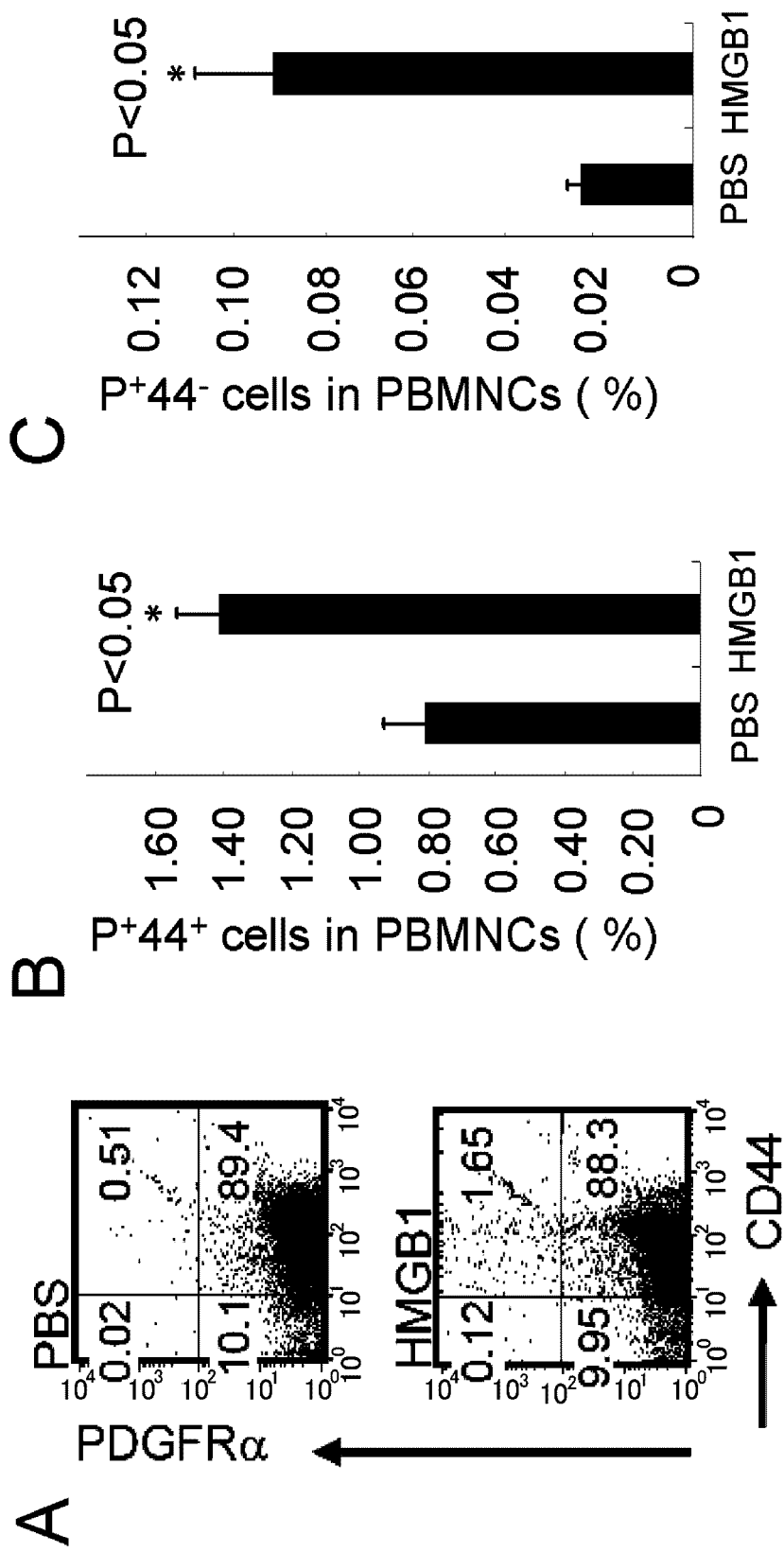
FIG. 14A shows in a diagram the flow cytometry result that shows the presence of cells having CD44 and PDGFRα. HMGB1 administration increased both populations of PDGFRα and CD44 double-positive cells, and PDGFRα-positive CD44-negative cells in peripheral blood.
FIGS. 14B and 14C show results of comparison between the PBS- and HMGB1- administered groups on the presence of PDGFRα and CD44 double-positive cells, and PDGFRα-positive CD44-negative cells in peripheral blood, respectively. Both cell populations were statistically significantly increased in the HMGB1-administered group.

Results: PDGFRα and CD44 double-positive cells, and PDGFRα-positive, CD44-negative cells in the peripheral blood mononuclear cell fraction were demonstrated to be significantly increased 12 hours after HMGB1 administration (FIG. 14). Specifically, HMGB1 was demonstrated to have the activity of mobilizing PDGFRα-positive cells to peripheral blood from bone marrow. PDGFRα is known as a mesenchymal stem cell marker.

Discussion: PDGFRα and CD44 are known as surface markers of bone marrow mesenchymal stem cells, which are representative of bone marrow-derived pluripotent stem cells. Bone marrow mesenchymal stem cells are pluripotent stem cells capable of differentiating into nerve cells, epithelial cells, or such as well as osteocytes, chondrocytes, and adipocytes. Meanwhile, the skin pieces used in this experiment are in an ischemic condition. Thus, the tissues gradually necrotize and intracellular proteins such as nuclear proteins as well as cell surface proteins are released to the outside. HMGB1 is a protein contained in the skin extract. In skin grafting or the like, such proteins serve as a signal to mobilize bone marrow-derived tissue stem cells into grafted skin. It is thus speculated that functional skin regeneration is achieved in the skin graft due to reconstitution of epidermis, hypodermis, follicular tissues, or such stemmed from the bone marrow cells. Based on this experiment, the present invention for the first time successfully discovered that bone marrow-derived tissue stem cells are mobilized into peripheral blood circulation by intravenous administration of HMGB1 or skin extract as described above. This discovery enables new therapeutic methods for treating intractable diseases with tissue damages such as brain infarction, myocardial infarction, bone fracture, and cutaneous ulcer, which are based on mobilization of bone marrow-derived pluripotent stem cells into peripheral blood. In addition, cells mobilized to peripheral blood can be collected in the same way as conventional method for blood collection. Thus, the present invention enables simpler and safer methods for collecting bone marrow-derived tissue stem cells as compared to the conventional method for treating brain infarction in which cells are collected from the bone marrow.

Reference Example 1

Objective: Identification of the HMGB1 family in the skin extract and examination of bone marrow mesenchymal stem cell-inducing activity Methods: Whether or not the neonatal mouse skin extract contained the HMGB protein family was confirmed using the Western blot method. Free skin pieces from 400 neonatal mice were immersed in 400 ml of physiological phosphate buffer solution (PBS; pH 7.4) and the solution was incubated at 4° C. for 24 hours. To remove the tissues, the samples were centrifuged at 440 G at 4° C. for 10 minutes and the supernatant was collected as skin extract. Ten µl of the skin extract obtained was used as a sample and subjected to SDS-PAGE electrophoresis. The proteins separated within the gel were transferred onto a PVDF membrane using a blotting device (ATTO). The membrane was incubated with PBS containing 3% skim milk and 0.1% Tween20 (S-T-PBS) at room temperature for one hour, and then was allowed to react with each of rabbit anti-mouse HMGB1 antibody, rabbit anti-mouse HMGB2 antibody, or rabbit anti-mouse HMGB3 antibody which were diluted 1.000-fold with S-T-PBS, at 4° C. for 16 hours. After the reaction, the PVDF membrane was washed with S-T-PBS five times for 5 minutes. Then, the PVDF membrane was incubated with 2.000-fold diluted (diluted with S-T-PBS) peroxidase-labeled goat anti-rabbit IgG antibody (GE Healthcare) at 25° C. for 1 hour. Further, after washing with S-T-PBS five times for 5 minute, the PVDF membrane was allowed to react with ECL Western Blotting Detection System (GE Healthcare). The ECL film was exposed and developed to detect the presence of HMGB1, HMGB2, and HMGB3 proteins.

RNA was extracted from the skin of neonatal mouse using Trizol (Invitrogen), and further cDNA was synthesized using the SuperScript III cDNA Synthesis Kit (Invitrogen). Using this cDNA as a template, cDNAs of HMGB1, HMGB2, and HMGB3 were amplified using the polymerase chain reaction (PCR) method. The cDNAs were inserted into the plasmid vector pCAGGS for expressing proteins in mammalian cells, such that proteins with an additional Flag-tag sequence (Asp-Tyr-Lys-Asp-Asp-Asp-Lys; SEQ ID: 18) at the N-terminus of the amino acid sequence could be expressed. These plasmid vectors were transfected into HEK293 (Human embryonic kidney derived culture cell line) and cultured for 48 hours to express the proteins. Cells expressing each of the HMGB1, HMGB2, and HMGB3 proteins and the culture supernatant were incubated at 4° C. for 16 hours, which was then centrifuged at 4,400 g for 5 minutes to collect the supernatant. 100 µL of the anti-Flag antibody Gel (Sigma) was mixed into 50 mL of this supernatant, and was then incubated at 4° C. for 16 hours. Centrifugation was then performed to collect the gel, and was washed with PBS five times. Further, the protein was eluted using 3× Flag peptide (final 100 μg/ml). Expressions of recombinant proteins were observed by the Western blot method using 1,000-fold diluted (diluted with S-T-PBS) mouse anti-Flag antibody and 2,000-fold diluted (diluted with S-T-PBS) peroxidase-labeled anti-mouse IgG antibody (GE Healthcare). The mouse bone marrow mesenchymal stem cell migration activity in these purified recombinant proteins was assessed using a Boyden chamber. Moreover, in order to observe the in vivo drug efficacy of the HMGB family, the dorsal skin of 8-week-old C57BL/6 mice was cut out in a circle having a diameter of 8 μm to prepare cutaneous ulcer models. Purified HMGB1, HMGB2, and HMGB3 (100 ng/μl) were each mixed with the same amount of hyaluronic acid solution having a concentration of 1 g/100 mL of PBS, and 100 μL of it was administered to the ulcer surface. The ulcer surface was covered with a transparent adhesive wound dressing/protective material Tegaderm (3M Healthcare) to avoid drying, and the wound area was measured over time to determine the therapeutic effect.

Further, to examine whether or not the human skin extract and the purified human HMGB1 has an activity to allow migration of human bone marrow mesenchymal stem cells, a Boyden chamber was used for assessment. A human skin having an area of 1 cm² was immersed in 1 ml PBS, and then was incubated at 4° C. for 16 hours and subsequently centrifuged at 440 G at 4° C. for 10 minutes. The supernatant alone was collected to be used as a human skin extract. Moreover, human bone marrow mesenchymal stem cells (Cambrex) were used as the cells to be placed in the upper chamber of the Boyden chamber (as a result of surface antigen analysis by flow cytometry, these cells have been confirmed to be CD105-positive, CD166-positive, CD29-positive, CD44-positive, CD34-negative, and CD45-negative. They have also been found to differentiate into adipocytes, chondrocytes, and osteocytes by differentiation induction tests). Moreover, 100 ng/well of human HMGB1 (R&D) and human skin extract diluted 10-fold with PBS were placed in the lower chamber. PBS was used as a control.

Figure 6:
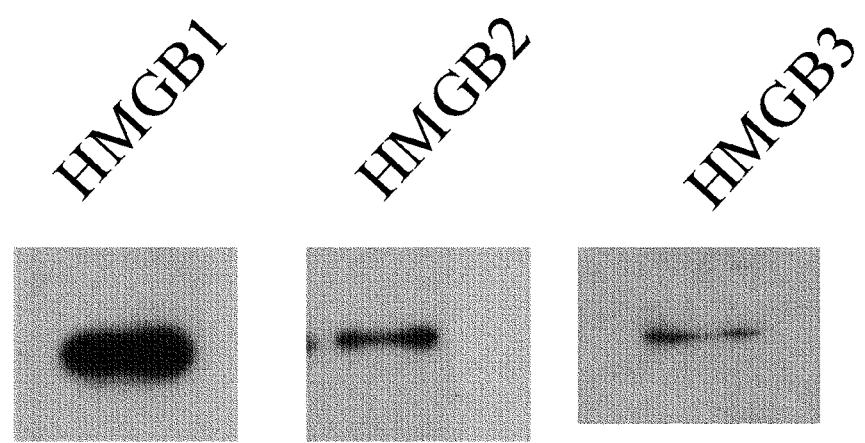
FIG. 6 shows in a set of photographs Western blot detection of the HMGB family in neonatal mouse skin extract.
Figure 7:
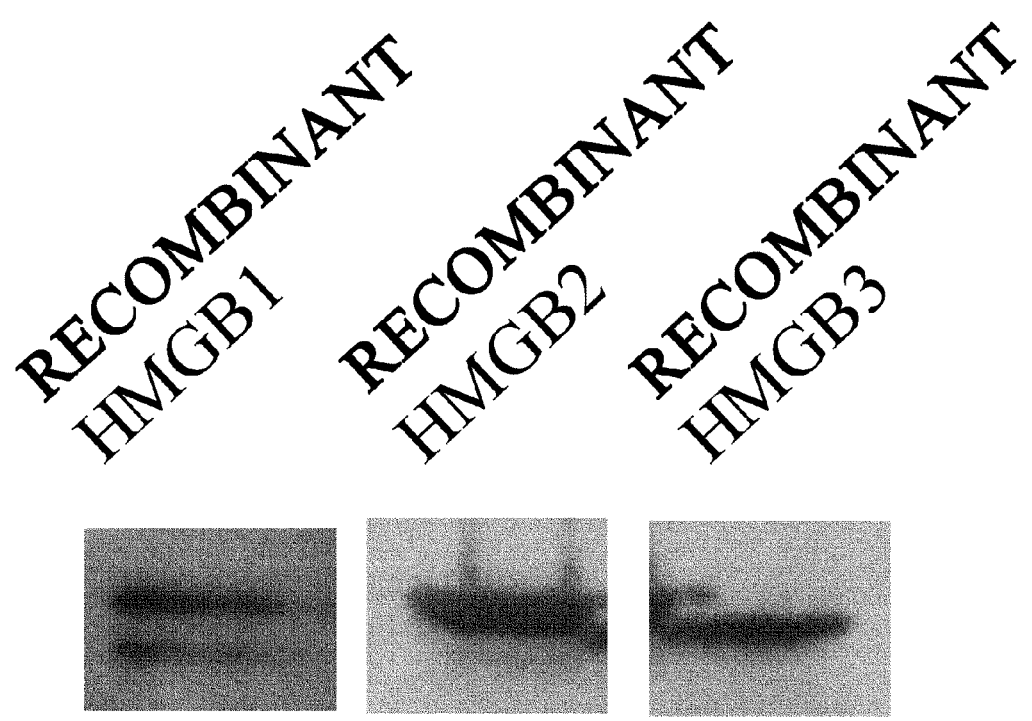
FIG. 7 shows in a set of photographs Western blot results for the purified recombinant Flag tag-HMGB family-fusion proteins expressed in HEK293 cells.
Figure 8:
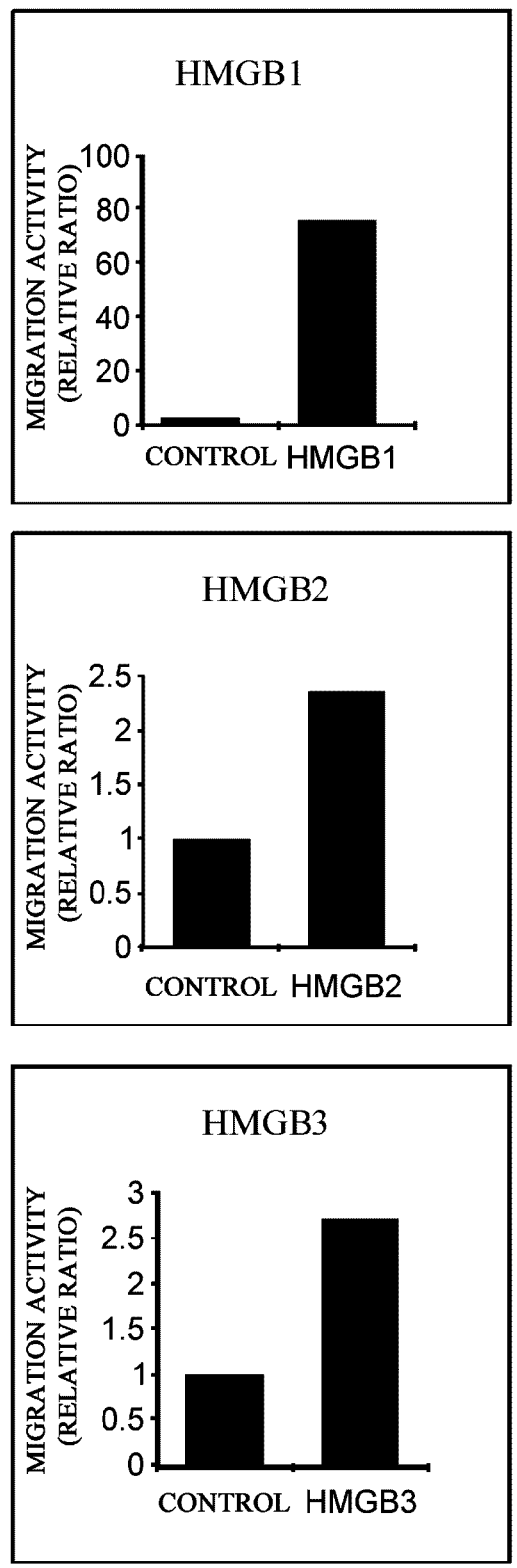
FIG. 8 presents a set of graphs showing the migration activity of bone marrow mesenchymal stem cells by recombinant HMGB1/HMGB2/HMGB3 using a Boyden chamber. All recombinant proteins showed higher migration activities as compared to the control groups.
Figure 9:
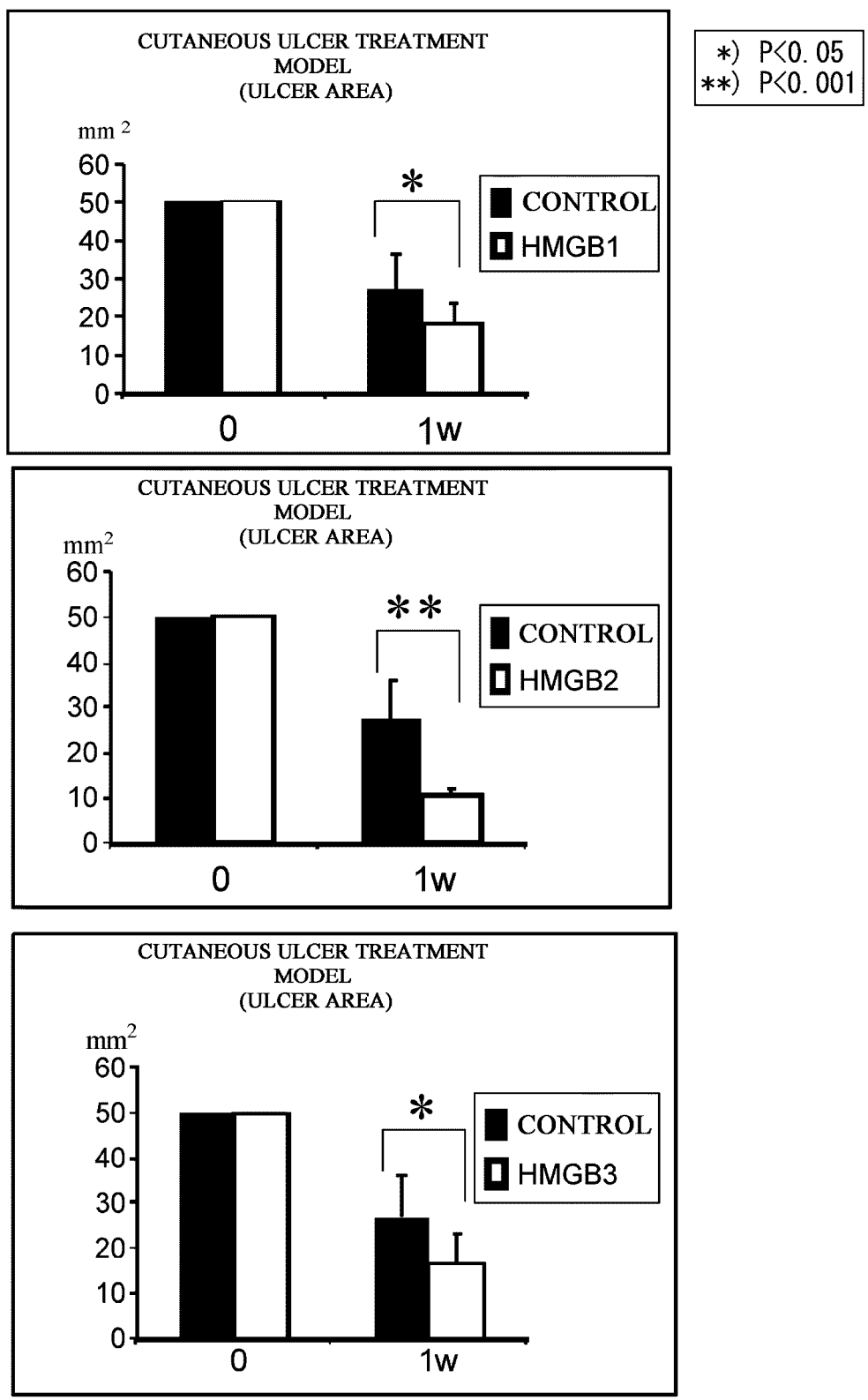
FIG. 9 shows in a set of graphs the result of treatment in a mouse cutaneous ulcer treatment model using the HMGB family proteins. HMGB1, HMGB2, and HMGB3 all showed significant effects on reducing the ulcer area as compared to the control groups.
Figure 10:
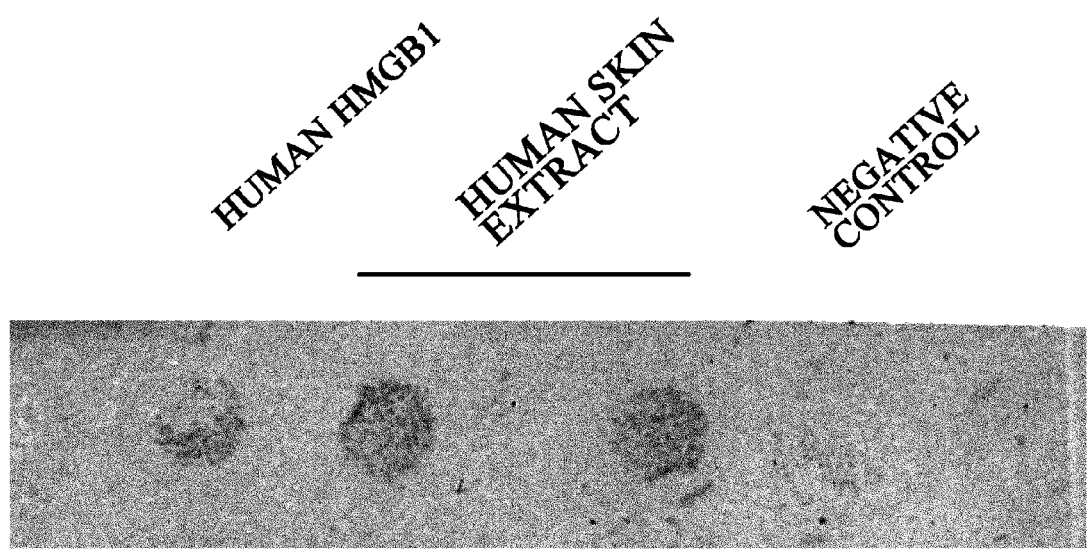
FIG. 10 shows in a photograph the activity of human HMGB1 and a human skin extract to induce the migration of human bone marrow-derived mesenchymal stem cells as confirmed using a Boyden chamber.

Results: As a result of Western blotting, bands of HMGB2 and HMGB3 were detected as well as the HMGB1 band. Therefore, the neonatal mouse skin extract was confirmed to contain the family proteins, HMGB2 and HMGB3, besides HMGB1 (FIG. 6). Expression vectors of HMGB1/HMGB2/HMGB3 having a Flag-tag added at the N-terminus of each protein were prepared (FIG. 1). These expression vectors were transfected into HEK293 cells, and the expressed proteins were purified using the Flag-tag, and Western blotting was carried out to observe these proteins (FIG. 7). The mouse bone marrow mesenchymal stem cell migration activity was measured using these purified proteins, and the activity was confirmed in all of the proteins (FIG. 8). The ulcer area produced in the back of the mouse was measured every 7 days, and a significant effect on reducing ulcer area was confirmed in the HMGB1, 2, and 3 treatment groups, as compared to the untreated group (FIG. 9). Similar to the mouse case, human HMGB1 and the human skin extract were revealed to have the activity of inducing the migration of human bone marrow mesenchymal stem cell (FIG. 10).

Discussion: HMGB2 and HMGB3 are known as proteins having high homologies to HMGB1. These proteins are also expected to have properties similar to HMGB1. It was confirmed that HMGB2 and HMGB3 of the HMGB1 family are also produced from the extract of the free skin section. Further, HMGB1/HMGB2/HMGB3 recombinant proteins were produced, and their in vitro bone marrow mesenchymal stem cell migration activity and the in vivo therapeutic effect on a cutaneous ulcer were also confirmed. It was revealed that the HMGB family (HMGB1/HMGB2/HMGB3) and the recombinant HMGB family in the neonatal mouse free skin section have a bone marrow mesenchymal stem cell-inducing activity and an activity of locally inducing bone marrow-derived stem cells which are differentiatable into epithelium, and that the thus induced bone marrow-derived cell group differentiates into various cells such as epidermal keratinocytes, hair follicles, and fibroblasts in the damaged tissue to promote the recovery of the damaged tissue. Moreover, since bone marrow mesenchymal stem cells are multipotent stem cells, the present inventors believe that therapeutic effects can also be expected in the same manner by systematic administration or local administration of the HMGB family to treat damaged states in other tissues, for example, tissue damages such as brain injury, myocardial infarction, and bone fracture.

Moreover, it is known that, between human and mouse, amino acid sequence homology for HMGB1 is 98% (213/215), 96% (202/210) for HMGB2, and 97% (195/200) for HMGB3. Therefore, human HMGB and mouse HMGB are considered to have similar activities, and the results revealed that human skin extract and human HMGB1 have bone marrow mesenchymal stem cell-inducing activities in a manner same as those of mouse skin extract and mouse HMGB1.

Reference Example 2

Objective: Establishment of a method of producing a tissue extract containing bone marrow mesenchymal stem cell-inducing factors Methods: Brain, heart, intestine, kidney, and liver of a 6-week-old C57BL6 mouse and skin of a neonatal mouse were immersed in 1 ml of physiological phosphate buffer solution (PBS) at pH 7.4. The solutions were incubated at 4° C. for 24 hours, and then centrifuged at 440 G at 4° C. for 10 minutes to remove the tissues. The supernatants were collected to prepare tissue extracts. To confirm whether the thus obtained extract has a bone marrow-derived mesenchymal stem cell-inducing activity, the migration activity of bone marrow-derived mesenchymal stem cells was examined using a Boyden chamber. Moreover, the HMGB1 concentration contained in these samples was measured using an HMGB1 ELISA Kit (Shino-Test). Further, tissue extracts of the brain, heart, and skin were allowed to bind to a heparin affinity column, and the bone marrow-derived mesenchymal stem cell-inducing activity in the protein-bound fraction was confirmed using Boyden chamber.

Figure 11:
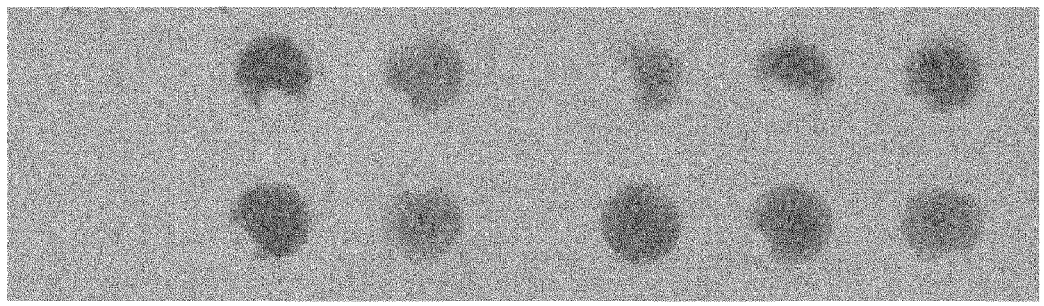
FIG. 11 shows in a set of photographs the activity of activators purified on a heparin column from mouse heart, brain, and skin extracts to induce bone marrow mesenchymal stem cells as confined using a Boyden chamber.
Figure 11:
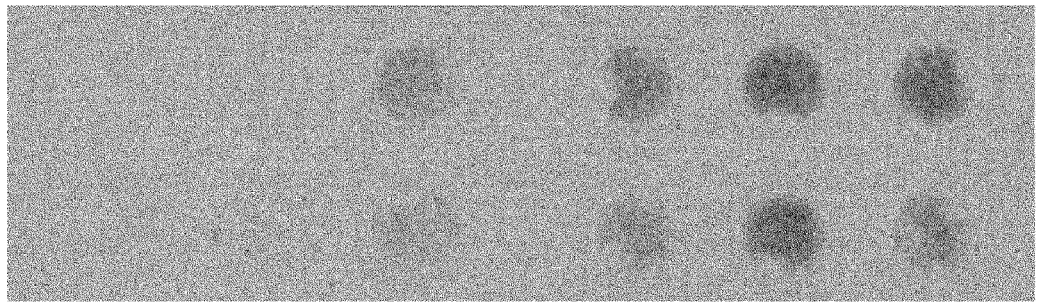

Results: The mouse brain extract contained an amount of HMGB1 equivalent to the neonatal mouse skin extract. Further, bone marrow mesenchymal stem cell-inducing activity was also observed in the mouse brain as well as in the skin. Although the mouse intestine extract and the mouse heart extract contained little HMGB1, bone marrow mesenchymal stem cell-inducing activities were observed. Moreover, the heparin column-bound fractions of mouse brain and mouse heart, as well as the heparin column-bound fraction of mouse skin, showed bone marrow mesenchymal stem cell-inducing activities (FIG. 11). Table 1 shows the measurement results of the HMGB1 concentration and the bone marrow mesenchymal stem cell-inducing activity in each of the mouse tissue extracts.

TABLE 1

| | HMGB1 concentration (ng/mL) | Bone marrow mesenchymal stem cell inducing activity |
|---|---|---|
| Skin | 110 | Present |
| Brain | 140 | Present |
| Heart | 4 | Present |
| Intestine | 0 | Present |
| Kidney | 115 | ND |
| Liver | 61 | ND |

ND: Not Determined

Discussion: A method in which HMGB1 can be conveniently extracted not only from the skin but also from the brain was developed by simply immersing these organs in a physiological buffer. This method is also applicable to other organs such as liver and kidney. Moreover, although the extracts from intestine and heart contain little HMGB1, a bone marrow mesenchymal stem cell-inducing activity was observed. This suggests these extracts contain other bone marrow mesenchymal stem cell-inducing substance(s) apart from HMGB1. Such substances contained in these extracts are originally present in each tissue, and are considered to physiologically induce bone marrow mesenchymal stem cells to the damaged tissue when the tissue is damaged. The present invention developed a novel method for conveniently and functionally extracting from various organs multiple bone marrow mesenchymal stem cell-inducing substances including HMGB1. Further, a method for purifying bone marrow mesenchymal stem cell-inducing substances from a tissue extract using the binding to the heparin column was also developed. These substances having bone marrow mesenchymal stem cell-inducing activities can be purified from the brain and heart in the same manner as in the skin using a heparin column.

Reference Example 3

Objective: Establishment of a method for extracting mesenchymal stem cell migration activators from cultured cells.

Methods: Human embryonic kidney derived cultured cell line HEK293 and human cervix carcinoma cell line HeLa were each cultured in 10% fetal bovine serum-containing D-MEM (Nacalai). These cells were each washed with PBS, and then $10^7$ cells were immersed in 5 ml of PBS (Nacalai) at 4° C. for 16 hours. The solution was centrifuged at 440 G (acceleration of gravity) at 4° C. for 5 minutes, and then the supernatant was collected. Human bone marrow mesenchymal stem cells were placed in the upper chamber of a Boyden chamber, and a 5-fold diluted (with DMEM) cell extract was placed in the lower chamber, to confirm the migration activity of human bone marrow mesenchymal stem cells.

Figure 12:
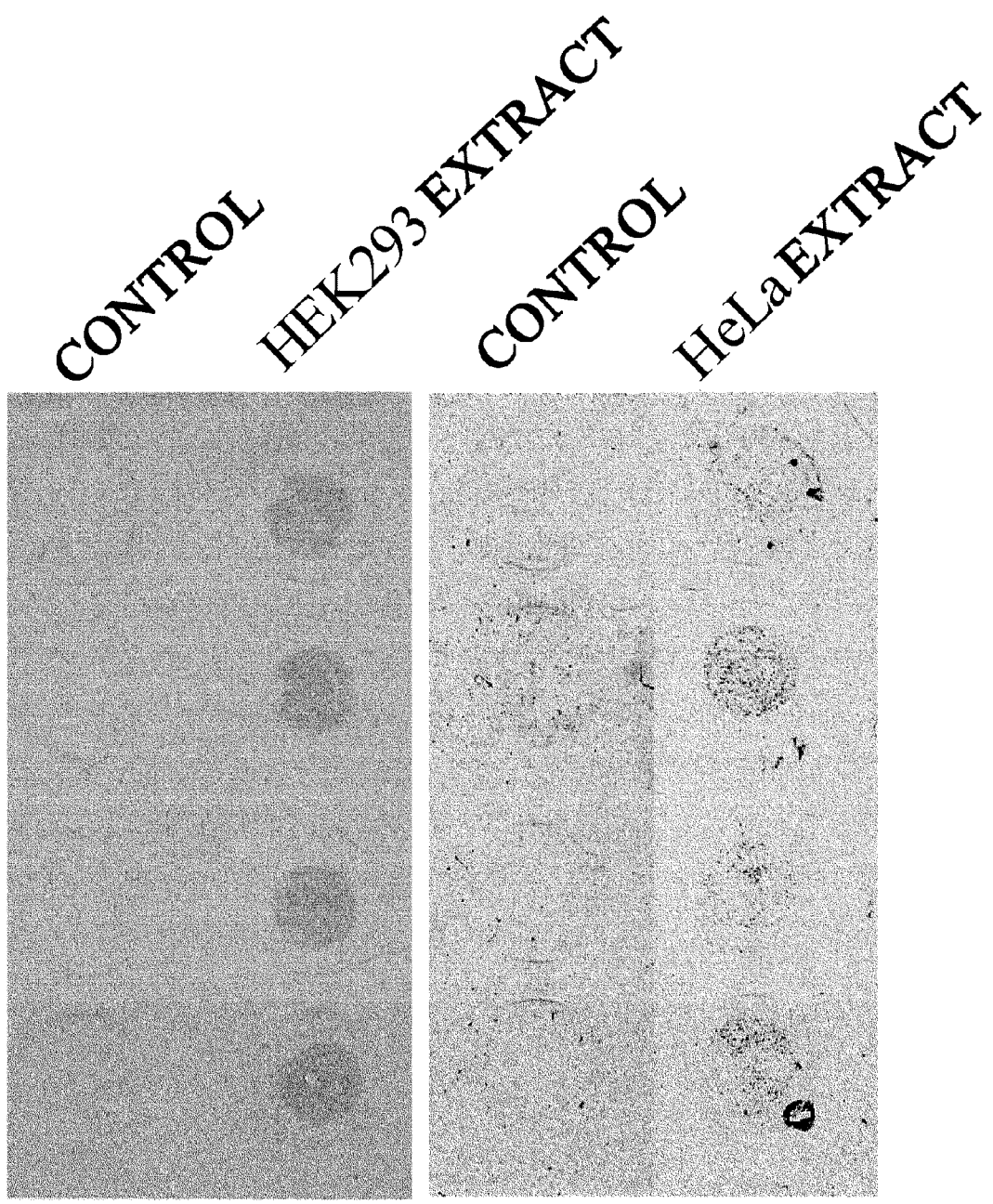
FIG. 12 shows in a set of photographs the activity of cultured cell line HEK293 extract and HeLa extract to induce the migration of human bone marrow mesenchymal stem cells as confirmed using a Boyden chamber. Both cultured cell lines showed chemotactic activity for human bone marrow mesenchymal stem cells.

Results: HEK293 extract and HeLa extract both showed similar bone marrow mesenchymal stem cell migration activities (FIG. 12).

Discussion: Bone marrow mesenchymal stem cell migration activators were successfully extracted by the convenient method of immersing cultured cells in PBS.

Reference Example 4

Objective: Whether or not regeneration of neural cells can be induced is examined by producing mouse brain-defective models, to which a heparin-column purified fraction of skin extract is administered in a sustained-release manner at the local lesion site, by which stem cells contained in a mouse myeloid system is allowed to migrate into the local lesion site.

Methods:
(1) Preparation of Heparin-Column Purified Fraction of Skin Extract

An excised skin section of a neonatal mouse was incubated in PBS (mouse/ml) at 4° C. for 16 hours, and a skin extract was obtained. The skin extract was diluted 10-fold with 9 volumes of 20 mM phosphate buffer at pH 7.5 at 4° C. 20 mM phosphate buffer at pH 7.5 (30 ml) was poured into HiTrap Hepalin HP column (column volume: 5 ml, GE Healthcare) in advance to equilibrate the column. The diluted solution was then allowed to bind to the column. Thereafter, the column was washed with 20 mM phosphate buffer at pH 7.5 and 100 mM NaCl (30 ml). To elute the adsorbed proteins, 20 mM phosphate buffer at pH 7.5 and 1,000 mM NaCl were poured into the column, and the factions were eluted into the tubes. Each of the adsorbed factions were evaluated according to the mouse bone marrow-derived cell migration activity assessment using the Boyden chamber method, and fraction(s) having migratory activity was collected. Solution(s) having the activity was used as a heparin purified fraction(s) of the skin extract in the following Reference Example.

(2) Production of Myelosuppressive Mice

Mice were irradiated with single-dose of X-ray at 10 Gy to produce myelosuppressive mice.

(3) Transplantation of GFP Mouse Bone Marrow to Myelosuppressive Mice

Bone marrow cells were collected from both femurs and crus bones of GFP mice. These cells were administered to the myelosuppressive mice through the caudal vein 24 hours after the irradiation. The administration was carried out under inhalational anesthesia using isoflurane.

(4) Production of a Brain-Defective (Brain Tissue-Defective) Mouse Model

Figure 13:
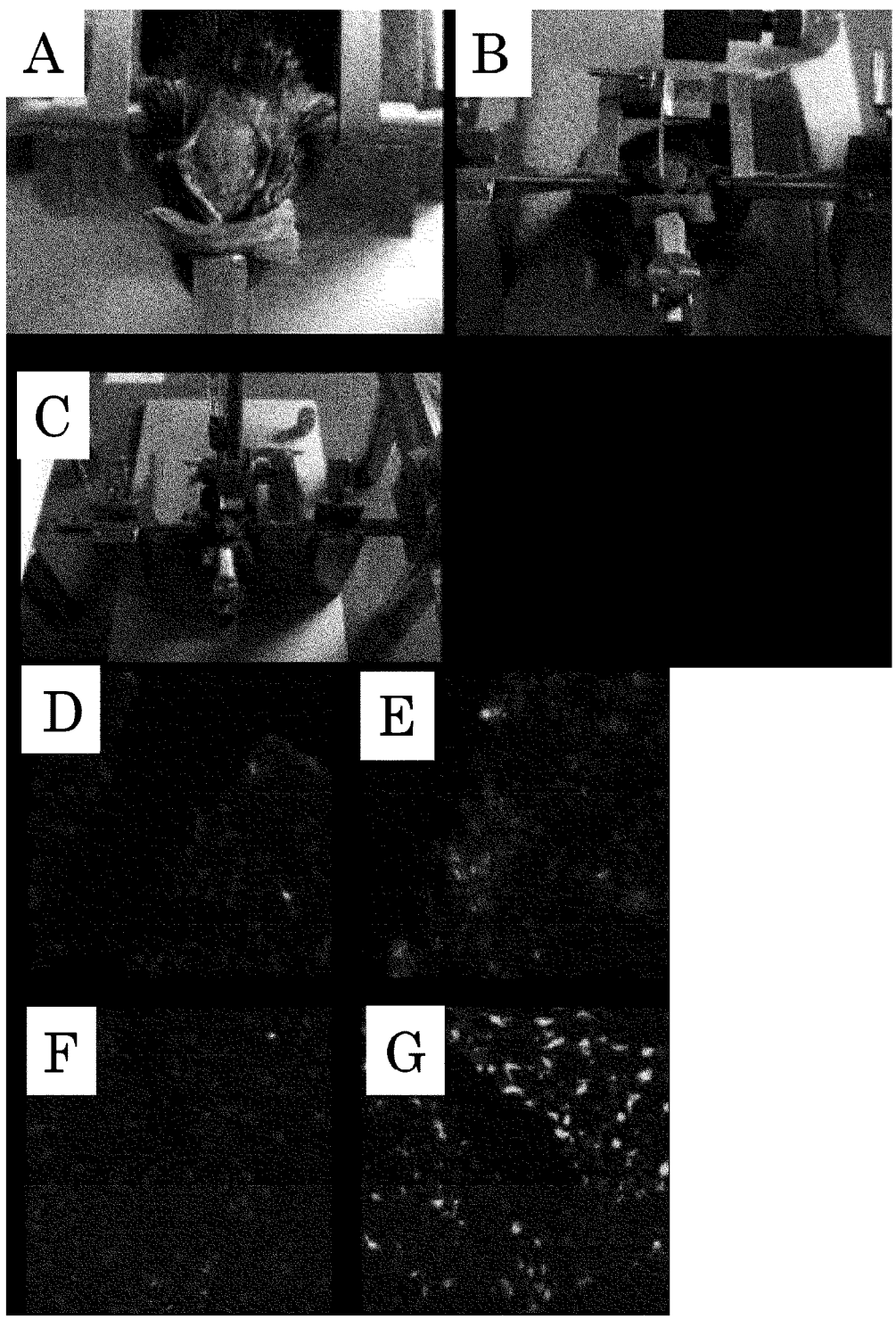
FIG. 13A shows in a photograph a mouse fixed to a brain stereotaxic apparatus and subjected to a midline incision in the head with a scalpel, followed by trepanation using a drill.
FIG. 13B is a photograph showing the brain to which a negative pressure is applied using a syringe to suck part of the brain tissue.
FIG. 13C is a photograph of a mouse after injection of 5 μl heparin-column purified fraction of a skin extract dissolved in fibrin adhesive formulation (fibrinogen), and a subsequent injection of 5 μl of fibrin glue formulation (thrombin).
FIGS. 13D and 13E are photographs of the brain injury model taken 2 weeks after the treatment. Higher accumulation of GFP-positive cells was observed in the treatment group using the heparin-column purified fraction of skin extract in E compared to the control in D.
FIGS. 13F and 13G are photographs of the brain injury model taken 6 weeks after the treatment. Higher accumulation of GFP-positive cells was observed in the treatment group using the heparin-column purified fraction of skin extract in G compared to the control in F.

The myelosuppressive mice transplanted with GFP mouse bone marrow cells were subjected to inhalational anesthesia using isoflurane, and pentobarbital (45 mg/kg) was intraperitoneally injected to the mice. The mice were fixed onto a brain stereotaxis apparatus and subjected to a midline incision in the head with a scalpel. Trepanation was carried out at 2.5 mm right-lateral and 12.5 mm anterior to the bregma using a drill (FIG. 13A). At a 3 mm depth from this site, a 20 G Surflow needle was inserted and fixed. Then, a negative pressure was applied using a syringe to suck part of the brain tissue (FIG. 13B).

(5) Administration of a Heparin-Column Purified Fraction of Skin Extract to the Brain Tissue-Defective Site Five microliters of a heparin-column purified fraction of skin extract dissolved in a fibrin tissue adhesive formulation (fibrinogen) (Bolheal (Kaketsuken)) was injected to the above site, and subsequently, 5 μl of a fibrin tissue adhesive formulation (thrombin) (Bolheal (Kaketsuken)) was injected using a Hamilton syringe and a 26 G syringe (FIG. 13C). The aim of this operation was to exert the sustained-release agent effect of a heparin-column-purified fraction of the skin extract.

(6) Assessment of the Effects of Neural Cell Regeneration in Brain Tissue-Defective Sites Mice of the control group and the treatment group were used for the assessment. An appropriate elapsed time setting (over time) was determined, the mice were perfused with 4% paraformaldehyde and fixed and then the brain was cut out. Further, external fixation was performed with 4% paraformaldehyde. These were then dehydrated in a 15% and 30% sucrose gradient to produce frozen sections.

The nucleus were stained with a DAPI (4',6-Diamidino-2-phenylindole, dihydrochloride) solution and the section was sealed using a photobleaching inhibitor. The accumulation of GFP-positive cells in the lesion site (brain tissue-defective site) was assessed using a confocal laser microscope.

Results: The accumulation of GFP-positive cells is qualitatively shown for 2 weeks, and 6 weeks after the administration. The accumulation of GFP-positive cells tends to be higher in the lesion sites of the treatment group rather than the control group, for both 2 weeks (control; FIG. 13D, skin extract heparin-column-purified fraction; FIG. 13E) and 6 weeks (control; FIG. 13F, skin extract heparin-column-purified fraction; FIG. 13G) after the administration.

Discussion: The administration of the heparin-column-purified fraction of the skin extract resulted in the accumulation of bone marrow-derived cells in the brain tissue-defective site, which showed a nerve cell form. Bone marrow-derived mesenchymal stem cells are also known to differentiate into nerve cells and the result revealed that the heparin-column purified fraction of the skin extract is capable of inducing neural cell regeneration of the injured site in the brain. Moreover, this is also applicable to neuronal regeneration of damaged sites in brain tissues in cerebral ischemic diseases and cerebral contusions.

Industrial Applicability

The present invention provides novel therapeutic methods for treating intractable diseases with tissue damages such as brain infarction, myocardial infarction, bone fracture, and cutaneous ulcer. In addition, cells mobilized to peripheral blood can be collected in the same way as a conventional method for blood collection. Thus, the present invention enables simpler and safer methods for collecting bone marrow-derived tissue stem cells as compared to the conventional method used to treat brain infarction in which cells are collected from the bone marrow.

---

The invention claimed is:

1. A method of mobilizing a bone marrow mesenchymal stem cell to peripheral blood from bone marrow, comprising the steps of administering to blood vessel or muscle of a living animal one or more substances selected from the group consisting of:
   (a) an HMGB1 protein;
   (b) a cell that secretes an HMGB1 protein;
   (c) a vector inserted with a DNA encoding an HMGB1 protein;
   (d) an HMGB2 protein;
   (e) a cell that secretes an HMGB2 protein;
   (f) a vector inserted with a DNA encoding HMGB2 protein;
   (g) an HMGB3 protein;
   (h) a cell that secretes an HMGB3 protein; and
   (i) a vector inserted with a DNA encoding an HMGB3 protein; and mobilizing a bone marrow mesenchymal stem cell to peripheral blood from bone marrow.

2. The method according to claim 1, wherein one or more substances selected from (a) to (i) are administered to blood vessel.

3. The method according to claim 2, wherein one or more substances selected from (a) to (i) are administered via intravascular injection.

4. The method according to claim 3, wherein one or more substances selected from (a) to (i) are administered via intraarterial injection or intravenous injection.

5. The method according to claim 1, wherein one or more substances selected from (b) to (i) are administered.

6. The method according to claim 1, wherein one or more substances from (d) to (i) are administered.

7. The method according to claim 1, wherein the living animal is human.

* * * * *